United States Patent
Barone et al.

(10) Patent No.: US 11,779,702 B2
(45) Date of Patent: Oct. 10, 2023

(54) METHOD FOR DYNAMIC PRESSURE CONTROL IN A FLUID INJECTOR SYSTEM

(71) Applicant: BAYER HEALTHCARE LLC, Whippany, NJ (US)

(72) Inventors: William Barone, Pittsburgh, PA (US); Michael Spohn, Fenelton, PA (US); Chelsea Marsh, Pittsburgh, PA (US); Michael McDermott, Pittsburgh, PA (US); John Volkar, Valencia, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 543 days.

(21) Appl. No.: 16/621,289

(22) PCT Filed: Aug. 28, 2018

(86) PCT No.: PCT/US2018/048283
§ 371 (c)(1),
(2) Date: Dec. 11, 2019

(87) PCT Pub. No.: WO2019/046260
PCT Pub. Date: Mar. 7, 2019

(65) Prior Publication Data
US 2020/0114074 A1    Apr. 16, 2020

Related U.S. Application Data

(60) Provisional application No. 62/552,433, filed on Aug. 31, 2017.

(51) Int. Cl.
*A61M 5/168* (2006.01)
*A61M 5/00* (2006.01)
(Continued)

(52) U.S. Cl.
CPC ........ *A61M 5/16827* (2013.01); *A61M 5/007* (2013.01); *A61M 5/1408* (2013.01);
(Continued)

(58) Field of Classification Search
CPC .............. A61M 5/16827; A61M 5/007; A61M 5/1408; A61M 5/14546; A61M 5/14566;
(Continued)

(56) References Cited

U.S. PATENT DOCUMENTS 383,858 A    6/1888 Campbell
508,584 A    11/1893 Stevens
(Continued)

FOREIGN PATENT DOCUMENTS

CA    2045070 A1    2/1992
CA    2077712 A1    12/1993
(Continued)

OTHER PUBLICATIONS

Swiss; Medical Care., "CT Expres Contrast Media Delivery System Operation Manual Rev 1", 2004.
(Continued)

*Primary Examiner* — Lauren P Farrar
*Assistant Examiner* — Hamza A Darb
(74) *Attorney, Agent, or Firm* — Joseph L. Kent; James R. Stevenson; David Schramm

(57) ABSTRACT

A method for dynamic pressure control during a multiphase injection is described wherein the pressures of fluids in the various reservoirs of a fluid delivery system are controlled to provide desired fluid delivery parameters. The methods include advancing the first drive member to expel the first fluid from the first reservoir into a conduit, wherein the fluid is pressurized to a first fluid pressure; measuring the first fluid pressure to provide a target value; while the second reservoir is in fluid isolation from the conduit, advancing or
(Continued)

retracting the second drive member to increase or decrease the fluid pressure of the second fluid in the second reservoir to the target value; placing the second reservoir in fluid communication with the conduit; and advancing the second drive member to expel the second fluid from the second reservoir into the conduit.

22 Claims, 12 Drawing Sheets

(51) Int. Cl.
| | |
|---|---|
| A61M 5/14 | (2006.01) |
| A61M 5/145 | (2006.01) |
| A61M 5/142 | (2006.01) |
| G21C 7/10 | (2006.01) |
| G21C 7/24 | (2006.01) |
| G21C 1/08 | (2006.01) |
| G21C 3/07 | (2006.01) |
| G21C 3/328 | (2006.01) |
| G21C 11/08 | (2006.01) |
| C23C 30/00 | (2006.01) |

(52) U.S. Cl.
CPC .... *A61M 5/14546* (2013.01); *A61M 5/14566* (2013.01); *A61M 5/16854* (2013.01); *G21C 7/10* (2013.01); *G21C 7/24* (2013.01); *A61M 2005/14208* (2013.01); *A61M 2205/3341* (2013.01); *C23C 30/00* (2013.01); *G21C 1/08* (2013.01); *G21C 3/07* (2013.01); *G21C 3/328* (2013.01); *G21C 11/08* (2013.01)

(58) Field of Classification Search
CPC .... A61M 5/16854; A61M 2005/14208; A61M 2205/3341; A61M 2005/14506; A61M 5/16809; G21C 7/10; G21C 7/24; G21C 1/08; G21C 3/07; G21C 3/328; G21C 11/08; C23C 30/00
See application file for complete search history.

(56) References Cited

U.S. PATENT DOCUMENTS

| | | |
|---|---|---|
| 945,143 A | 1/1910 | Iacques |
| 2,511,291 A | 6/1950 | Mueller |
| 2,583,206 A | 1/1952 | Borck et al. |
| 3,156,236 A | 11/1964 | Williamson |
| 3,159,312 A | 12/1964 | Van Sciver, II |
| 3,276,472 A | 10/1966 | Jinkens et al. |
| 3,349,713 A | 10/1967 | Fassbender |
| 3,520,295 A | 7/1970 | Kelly |
| 3,523,523 A | 8/1970 | Heinrich et al. |
| 3,623,474 A | 11/1971 | Heilman |
| 3,635,444 A | 1/1972 | Potter |
| 3,671,208 A | 6/1972 | Wayne |
| 3,701,345 A | 10/1972 | Heilman |
| 3,719,207 A | 3/1973 | Takeda |
| 3,755,655 A | 8/1973 | Senecal |
| 3,793,600 A | 2/1974 | Grosbard |
| 3,812,843 A | 5/1974 | Wootten et al. |
| 3,817,843 A | 6/1974 | Barrett |
| 3,839,708 A | 10/1974 | Lyons et al. |
| 3,868,967 A | 3/1975 | Harding |
| 3,888,239 A | 6/1975 | Rubinstein |
| 3,895,220 A | 7/1975 | Nelson et al. |
| 3,898,983 A | 8/1975 | Elam |
| 3,927,955 A | 12/1975 | Spinosa et al. |
| 3,941,126 A | 3/1976 | Dietrich et al. |
| 3,958,103 A | 5/1976 | Oka et al. |
| 3,968,195 A | 7/1976 | Bishop |
| 3,995,381 A | 12/1976 | Manfred et al. |
| 4,001,549 A | 1/1977 | Corwin |
| 4,006,736 A | 2/1977 | Kranys et al. |
| 4,038,981 A | 8/1977 | Lefevre et al. |
| 4,044,757 A | 8/1977 | Mcwhorter et al. |
| 4,090,502 A | 5/1978 | Tajika |
| 4,135,247 A | 1/1979 | Gordon et al. |
| 4,151,845 A | 5/1979 | Clemens |
| 4,187,057 A | 2/1980 | Xanthopoulos |
| 4,191,183 A | 3/1980 | Mendelson |
| 4,199,000 A | 4/1980 | Edstrom |
| 4,204,775 A | 5/1980 | Speer |
| 4,207,871 A | 6/1980 | Jenkins |
| 4,208,136 A | 6/1980 | King et al. |
| 4,223,675 A | 9/1980 | Williams |
| 4,262,824 A | 4/1981 | Hrynewycz |
| 4,263,916 A | 4/1981 | Brooks et al. |
| 4,280,494 A | 7/1981 | Cosgrove, Jr. et al. |
| 4,284,073 A | 8/1981 | Krause et al. |
| 4,315,247 A | 2/1982 | Germanton |
| 4,319,568 A | 3/1982 | Tregoning |
| 4,329,067 A | 5/1982 | Goudy, Jr. |
| 4,340,153 A | 7/1982 | Spivey |
| 4,341,153 A | 7/1982 | Bowser |
| 4,392,847 A | 7/1983 | Whitney et al. |
| 4,392,849 A | 7/1983 | Petre et al. |
| 4,396,385 A | 8/1983 | Kelly et al. |
| 4,402,310 A | 9/1983 | Kimura |
| 4,409,966 A | 10/1983 | Lambrecht et al. |
| 4,434,820 A | 3/1984 | Glass |
| 4,434,822 A | 3/1984 | Bellamy et al. |
| 4,441,823 A | 4/1984 | Power et al. |
| 4,444,198 A | 4/1984 | Petre |
| 4,447,230 A | 5/1984 | Gula et al. |
| 4,448,200 A | 5/1984 | Brooks et al. |
| 4,474,476 A | 10/1984 | Thomsen |
| 4,477,923 A | 10/1984 | Baumann et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,504,908 A | 3/1985 | Riederer et al. |
| 4,509,526 A | 4/1985 | Barnes et al. |
| 4,512,764 A | 4/1985 | Wunsch |
| 4,542,459 A | 9/1985 | Riederer |
| 4,544,949 A | 10/1985 | Kurihara |
| 4,551,133 A | 11/1985 | Zegers et al. |
| 4,552,130 A | 11/1985 | Kinoshita |
| 4,559,036 A | 12/1985 | Wunsch |
| 4,563,175 A | 1/1986 | Lafond |
| 4,578,802 A | 3/1986 | Itoh |
| 4,585,009 A | 4/1986 | Barker et al. |
| 4,585,941 A | 4/1986 | Bergner |
| 4,610,670 A | 9/1986 | Spencer |
| 4,610,790 A | 9/1986 | Reti et al. |
| 4,611,340 A | 9/1986 | Okazaki |
| 4,612,572 A | 9/1986 | Komatsu et al. |
| 4,625,494 A | 12/1986 | Iwatschenko et al. |
| 4,626,144 A | 12/1986 | Berner |
| 4,633,307 A | 12/1986 | Honda |
| 4,634,426 A | 1/1987 | Kamen |
| 4,636,144 A | 1/1987 | Abe et al. |
| 4,655,197 A | 4/1987 | Atkinson |
| 4,662,906 A | 5/1987 | Matkovich et al. |
| 4,672,651 A | 6/1987 | Horiba et al. |
| 4,676,776 A | 6/1987 | Howson |
| 4,682,170 A | 7/1987 | Kubota et al. |
| 4,689,670 A | 8/1987 | Okazaki |
| 4,710,166 A | 12/1987 | Thompson et al. |
| 4,723,261 A | 2/1988 | Janssen et al. |
| 4,750,643 A | 6/1988 | Wortrich |
| 4,754,786 A | 7/1988 | Roberts |
| 4,781,687 A | 11/1988 | Wall |
| 4,783,273 A | 11/1988 | Knutsson et al. |
| 4,789,014 A | 12/1988 | Digianfilippo et al. |
| 4,793,357 A | 12/1988 | Lindstrom |
| 4,795,429 A | 1/1989 | Feldstein |
| 4,798,590 A | 1/1989 | O'Leary et al. |
| 4,804,454 A | 2/1989 | Asakura et al. |
| 4,823,833 A | 4/1989 | Hogan et al. |
| 4,835,521 A | 5/1989 | Andrejasich et al. |
| 4,836,187 A | 6/1989 | Iwakoshi et al. |

(56) References Cited

U.S. PATENT DOCUMENTS

| | | |
|---|---|---|
| 4,838,856 A | 6/1989 | Mulreany et al. |
| 4,840,620 A | 6/1989 | Kobayashi et al. |
| 4,844,052 A | 7/1989 | Iwakoshi et al. |
| 4,853,521 A | 8/1989 | Claeys et al. |
| 4,854,301 A | 8/1989 | Nakajima |
| 4,854,324 A | 8/1989 | Hirschman et al. |
| 4,857,056 A | 8/1989 | Talonn |
| 4,874,359 A | 10/1989 | White et al. |
| 4,879,880 A | 11/1989 | Harrison |
| 4,880,014 A | 11/1989 | Zarowitz et al. |
| 4,887,208 A | 12/1989 | Schneider et al. |
| 4,887,554 A | 12/1989 | Whitford |
| 4,901,731 A | 2/1990 | Millar |
| 4,903,705 A | 2/1990 | Imamura et al. |
| 4,913,154 A | 4/1990 | Ermert et al. |
| 4,922,916 A | 5/1990 | Ermert et al. |
| 4,925,444 A | 5/1990 | Orkin et al. |
| 4,929,818 A | 5/1990 | Bradbury et al. |
| 4,935,005 A | 6/1990 | Haines |
| 4,936,832 A | 6/1990 | Vaillancourt |
| 4,943,279 A | 7/1990 | Samiotes et al. |
| 4,943,779 A | 7/1990 | Pedersen et al. |
| 4,943,987 A | 7/1990 | Asahina et al. |
| 4,946,256 A | 8/1990 | Woodruff |
| 4,946,439 A | 8/1990 | Eggers |
| 4,947,412 A | 8/1990 | Mattson |
| 4,950,245 A | 8/1990 | Brown et al. |
| 4,952,068 A | 8/1990 | Flint |
| 4,954,129 A | 9/1990 | Giuliani et al. |
| 4,965,726 A | 10/1990 | Heuscher et al. |
| 4,966,579 A | 10/1990 | Polaschegg |
| 4,976,687 A | 12/1990 | Martin |
| 4,978,335 A | 12/1990 | Arthur, III |
| 4,981,467 A | 1/1991 | Bobo, Jr. et al. |
| 4,995,064 A | 2/1991 | Wilson et al. |
| 5,002,055 A | 3/1991 | Merki et al. |
| 5,004,472 A | 4/1991 | Wallace et al. |
| 5,009,654 A | 4/1991 | Minshall et al. |
| 5,010,473 A | 4/1991 | Jacobs |
| 5,013,173 A | 5/1991 | Shiraishi |
| 5,018,173 A | 5/1991 | Komai et al. |
| 5,032,112 A | 7/1991 | Fairchild et al. |
| 5,034,987 A | 7/1991 | Fujimoto et al. |
| 5,040,537 A | 8/1991 | Katakura |
| 5,053,002 A | 10/1991 | Barlow |
| 5,054,044 A | 10/1991 | Audon et al. |
| 5,056,568 A | 10/1991 | Digianfilippo et al. |
| 5,059,171 A | 10/1991 | Bridge et al. |
| 5,059,173 A | 10/1991 | Sacco |
| 5,061,243 A | 10/1991 | Winchell et al. |
| 5,069,662 A | 12/1991 | Bodden |
| 5,078,683 A | 1/1992 | Sancoff et al. |
| 5,088,981 A | 2/1992 | Howson et al. |
| 5,100,380 A | 3/1992 | Epstein et al. |
| 5,104,374 A | 4/1992 | Bishko et al. |
| 5,104,387 A | 4/1992 | Pokorney et al. |
| 5,108,365 A | 4/1992 | Woods, Jr. |
| 5,111,492 A | 5/1992 | Klausz |
| 5,113,905 A | 5/1992 | Pruitt et al. |
| 5,123,056 A | 6/1992 | Wilson |
| 5,123,121 A | 6/1992 | Broersma |
| 5,125,018 A | 6/1992 | Asahina |
| 5,128,121 A | 7/1992 | Berg et al. |
| 5,133,336 A | 7/1992 | Savitt et al. |
| 5,135,000 A | 8/1992 | Akselrod et al. |
| 5,140,862 A | 8/1992 | Pappalardo |
| 5,150,292 A | 9/1992 | Hoffmann et al. |
| 5,166,961 A | 11/1992 | Brunnett et al. |
| 5,180,895 A | 1/1993 | Briggs et al. |
| 5,180,896 A | 1/1993 | Gibby et al. |
| 5,190,744 A | 3/1993 | Rocklage et al. |
| 5,191,878 A | 3/1993 | Iida et al. |
| 5,196,007 A | 3/1993 | Ellman et al. |
| 5,199,604 A | 4/1993 | Palmer et al. |
| 5,207,642 A | 5/1993 | Orkin et al. |
| 5,215,095 A | 6/1993 | Macvicar et al. |
| 5,228,070 A | 7/1993 | Mattson |
| 5,230,614 A | 7/1993 | Zanger et al. |
| 5,242,390 A | 9/1993 | Goldrath |
| 5,249,122 A | 9/1993 | Stritzke |
| 5,249,579 A | 10/1993 | Hobbs et al. |
| 5,262,946 A | 11/1993 | Heuscher |
| 5,267,174 A | 11/1993 | Kaufman et al. |
| 5,269,756 A | 12/1993 | Dryden |
| 5,273,537 A | 12/1993 | Haskvitz et al. |
| 5,274,218 A | 12/1993 | Urata et al. |
| 5,276,614 A | 1/1994 | Heuscher |
| 5,286,252 A | 2/1994 | Tuttle et al. |
| 5,287,273 A | 2/1994 | Kupfer et al. |
| 5,295,967 A | 3/1994 | Rondelet et al. |
| 5,300,031 A | 4/1994 | Neer et al. |
| 5,301,656 A | 4/1994 | Negoro et al. |
| 5,301,672 A | 4/1994 | Kalender |
| 5,304,126 A | 4/1994 | Epstein et al. |
| 5,310,997 A | 5/1994 | Roach et al. |
| 5,311,568 A | 5/1994 | McKee, Jr. et al. |
| 5,313,992 A | 5/1994 | Grabenkort |
| 5,317,506 A | 5/1994 | Coutre et al. |
| 5,328,463 A | 7/1994 | Barton et al. |
| 5,329,459 A | 7/1994 | Kaufman et al. |
| 5,334,141 A | 8/1994 | Carr et al. |
| 5,339,799 A | 8/1994 | Kami et al. |
| 5,349,625 A | 9/1994 | Born et al. |
| 5,349,635 A | 9/1994 | Scott |
| 5,352,979 A | 10/1994 | Conturo |
| 5,354,273 A | 10/1994 | Hagen |
| 5,361,761 A | 11/1994 | Van et al. |
| 5,362,948 A | 11/1994 | Morimoto |
| 5,368,562 A | 11/1994 | Blomquist et al. |
| 5,368,567 A | 11/1994 | Lee |
| 5,368,570 A | 11/1994 | Thompson et al. |
| 5,373,231 A | 12/1994 | Boll et al. |
| 5,376,070 A | 12/1994 | Purvis et al. |
| 5,378,231 A | 1/1995 | Johnson et al. |
| 5,382,232 A | 1/1995 | Hague et al. |
| 5,383,231 A | 1/1995 | Yamagishi |
| 5,383,858 A | 1/1995 | Reilly et al. |
| 5,385,540 A | 1/1995 | Abbott et al. |
| 5,388,139 A | 2/1995 | Beland |
| 5,392,849 A | 2/1995 | Matsunaga et al. |
| 5,400,792 A | 3/1995 | Hoebel et al. |
| 5,417,213 A | 5/1995 | Prince |
| 5,431,627 A | 7/1995 | Pastrone et al. |
| 5,433,704 A | 7/1995 | Ross et al. |
| 5,445,621 A | 8/1995 | Poli et al. |
| 5,450,847 A | 9/1995 | Kaempfe et al. |
| 5,453,639 A | 9/1995 | Cronin et al. |
| 5,456,255 A | 10/1995 | Abe et al. |
| 5,458,128 A | 10/1995 | Polanyi et al. |
| 5,459,769 A | 10/1995 | Brown |
| 5,460,609 A | 10/1995 | O'Donnell |
| 5,464,391 A | 11/1995 | Devale |
| 5,468,240 A | 11/1995 | Gentelia et al. |
| 5,469,769 A | 11/1995 | Sawada et al. |
| 5,469,849 A | 11/1995 | Sasaki et al. |
| 5,472,403 A | 12/1995 | Cornacchia et al. |
| 5,474,683 A | 12/1995 | Bryant et al. |
| 5,485,831 A | 1/1996 | Holdsworth et al. |
| 5,489,265 A | 2/1996 | Montalvo et al. |
| 5,494,036 A | 2/1996 | Uber, III et al. |
| 5,494,822 A | 2/1996 | Sadri |
| 5,496,273 A | 3/1996 | Pastrone et al. |
| 5,507,412 A | 4/1996 | Ebert et al. |
| 5,515,851 A | 5/1996 | Goldstein |
| 5,522,798 A | 6/1996 | Johnson et al. |
| 5,531,679 A | 7/1996 | Schulman et al. |
| 5,531,697 A | 7/1996 | Olsen et al. |
| 5,533,978 A | 7/1996 | Teirstein |
| 5,544,215 A | 8/1996 | Shroy, Jr. et al. |
| 5,547,470 A | 8/1996 | Johnson et al. |
| 5,552,130 A | 9/1996 | Kraus et al. |
| 5,553,619 A | 9/1996 | Prince |
| 5,560,317 A | 10/1996 | Bunyan et al. |
| 5,566,092 A | 10/1996 | Wang et al. |

(56) References Cited

U.S. PATENT DOCUMENTS

| | | |
|---|---|---|
| 5,569,181 A | 10/1996 | Heilman et al. |
| 5,569,208 A | 10/1996 | Woelpper et al. |
| 5,573,515 A | 11/1996 | Wilson et al. |
| 5,579,767 A | 12/1996 | Prince |
| 5,583,902 A | 12/1996 | Bae |
| 5,590,654 A | 1/1997 | Prince |
| 5,592,940 A | 1/1997 | Kampfe et al. |
| 5,601,086 A | 2/1997 | Pretlow, III et al. |
| 5,611,344 A | 3/1997 | Bernstein et al. |
| 5,616,124 A | 4/1997 | Hague et al. |
| 5,681,285 A | 10/1997 | Ford et al. |
| 5,687,208 A | 11/1997 | Bae et al. |
| 5,687,708 A | 11/1997 | Farnsworth et al. |
| 5,713,358 A | 2/1998 | Mistretta et al. |
| 5,724,976 A | 3/1998 | Mine et al. |
| 5,725,500 A | 3/1998 | Micheler |
| 5,739,508 A | 4/1998 | Uber, III |
| 5,743,266 A | 4/1998 | Levene et al. |
| 5,768,405 A | 6/1998 | Makram-Ebeid |
| 5,796,862 A | 8/1998 | Pawlicki et al. |
| 5,799,649 A | 9/1998 | Prince |
| 5,800,397 A | 9/1998 | Wilson et al. |
| 5,806,519 A | 9/1998 | Evans, III et al. |
| 5,808,203 A | 9/1998 | Nolan, Jr. et al. |
| 5,827,219 A | 10/1998 | Uber, III et al. |
| 5,827,504 A | 10/1998 | Yan et al. |
| 5,840,026 A | 11/1998 | Uber, III et al. |
| 5,843,037 A | 12/1998 | Uber, III |
| 5,846,517 A | 12/1998 | Unger |
| 5,865,744 A | 2/1999 | Lemelson |
| 5,873,861 A | 2/1999 | Hitchins et al. |
| 5,881,124 A | 3/1999 | Giger et al. |
| 5,882,343 A | 3/1999 | Wilson et al. |
| 5,902,054 A | 5/1999 | Coudray |
| 5,903,454 A | 5/1999 | Hoffberg et al. |
| 5,916,165 A | 6/1999 | Duchon et al. |
| 5,920,054 A | 7/1999 | Uber, III |
| 5,947,935 A | 9/1999 | Kazousky et al. |
| 5,987,347 A | 11/1999 | Khoury et al. |
| 5,988,587 A | 11/1999 | Duchon et al. |
| 6,046,225 A | 4/2000 | Maddock |
| 6,055,985 A | 5/2000 | Bae et al. |
| 6,056,902 A | 5/2000 | Hettinga |
| 6,063,052 A | 5/2000 | Uber, III et al. |
| 6,073,042 A | 6/2000 | Simonetti |
| 6,099,502 A | 8/2000 | Duchon et al. |
| 6,113,568 A | 9/2000 | Olaussen |
| 6,132,396 A | 10/2000 | Antanavich et al. |
| 6,149,627 A | 11/2000 | Uber, III |
| 6,186,146 B1 | 2/2001 | Glickman |
| 6,201,889 B1 | 3/2001 | Vannah |
| 6,221,045 B1 | 4/2001 | Duchon et al. |
| 6,236,706 B1 | 5/2001 | Hsieh |
| 6,248,093 B1 | 6/2001 | Moberg |
| 6,306,117 B1 | 10/2001 | Uber, III |
| 6,313,131 B1 | 11/2001 | Lawyer |
| 6,317,623 B1 | 11/2001 | Griffiths et al. |
| 6,322,535 B1 | 11/2001 | Hitchins et al. |
| 6,344,030 B1 | 2/2002 | Duchon et al. |
| 6,381,486 B1 | 4/2002 | Mistretta et al. |
| 6,387,098 B1 | 5/2002 | Cole et al. |
| 6,397,093 B1 | 5/2002 | Aldrich |
| 6,397,097 B1 | 5/2002 | Requardt |
| 6,402,697 B1 | 6/2002 | Calkins et al. |
| 6,423,719 B1 | 7/2002 | Lawyer |
| 6,442,418 B1 | 8/2002 | Evans, III et al. |
| 6,470,889 B1 | 10/2002 | Bae et al. |
| 6,471,674 B1 | 10/2002 | Emig et al. |
| 6,478,735 B1 | 11/2002 | Pope et al. |
| 6,503,226 B1 | 1/2003 | Martinell et al. |
| 6,520,930 B2 | 2/2003 | Critchlow et al. |
| 6,527,718 B1 | 3/2003 | Connor et al. |
| 6,554,819 B2 | 4/2003 | Reich |
| 6,556,695 B1 | 4/2003 | Packer et al. |
| 6,572,851 B2 | 6/2003 | Muramatsu et al. |
| 6,574,496 B1 | 6/2003 | Golman et al. |
| 6,575,930 B1 | 6/2003 | Trombley, III et al. |
| 6,597,938 B2 | 7/2003 | Liu |
| 6,626,862 B1 | 9/2003 | Duchon et al. |
| 6,635,030 B1 | 10/2003 | Bae et al. |
| 6,643,537 B1 | 11/2003 | Zatezalo et al. |
| 6,652,489 B2 | 11/2003 | Trocki et al. |
| 6,656,157 B1 | 12/2003 | Duchon et al. |
| 6,673,033 B1 | 1/2004 | Sciulli et al. |
| 6,685,733 B1 | 2/2004 | Dae et al. |
| 6,691,047 B1 | 2/2004 | Fredericks |
| 6,699,219 B2 | 3/2004 | Emig et al. |
| 6,731,971 B2 | 5/2004 | Evans et al. |
| 6,754,521 B2 | 6/2004 | Prince |
| 6,775,764 B1 | 8/2004 | Batcher |
| 6,776,764 B2 | 8/2004 | Pinsky |
| 6,866,653 B2 | 3/2005 | Bae |
| 6,876,720 B2 | 4/2005 | Tsuyuki |
| 6,879,853 B2 | 4/2005 | Meaney et al. |
| 6,983,590 B2 | 1/2006 | Roelle et al. |
| 7,094,216 B2 | 8/2006 | Trombley, III et al. |
| 7,267,666 B1 | 9/2007 | Duchon et al. |
| 7,267,667 B2 | 9/2007 | Hou et al. |
| 7,292,720 B2 | 11/2007 | Horger et al. |
| 7,351,221 B2 | 4/2008 | Trombley et al. |
| 7,553,294 B2 | 6/2009 | Lazzaro et al. |
| 7,553,295 B2 | 6/2009 | Susi |
| 7,563,249 B2 | 7/2009 | Schriver et al. |
| 7,666,169 B2 | 2/2010 | Cowan et al. |
| 7,688,057 B2 | 3/2010 | Foss et al. |
| 7,861,893 B2 | 1/2011 | Voegele et al. |
| 7,925,330 B2 | 4/2011 | Kalafut et al. |
| 8,007,487 B2 | 8/2011 | Patrick et al. |
| 8,147,464 B2 | 4/2012 | Spohn et al. |
| 8,162,903 B2 | 4/2012 | Reilly et al. |
| 8,295,914 B2 | 10/2012 | Kalafut et al. |
| 8,337,456 B2 | 12/2012 | Schriver et al. |
| 8,377,003 B2 | 2/2013 | Wagner |
| 8,403,909 B2 | 3/2013 | Spohn et al. |
| 8,439,863 B2 | 5/2013 | Fago et al. |
| 8,486,017 B2 | 7/2013 | Masuda et al. |
| 8,905,969 B2 | 12/2014 | Nystrom et al. |
| 8,945,051 B2 | 2/2015 | Schriver et al. |
| 9,101,708 B2 | 8/2015 | Small et al. |
| 9,173,995 B1 | 11/2015 | Tucker et al. |
| 9,199,033 B1 | 12/2015 | Cowan et al. |
| 9,238,099 B2 | 1/2016 | Kalafut et al. |
| 9,242,083 B2 | 1/2016 | Fago et al. |
| 9,259,527 B2 | 2/2016 | Spohn et al. |
| 9,314,749 B2 | 4/2016 | Yagi et al. |
| 9,333,293 B2 | 5/2016 | Williams, Jr. et al. |
| 9,474,857 B2 | 10/2016 | Riley et al. |
| 9,480,791 B2 | 11/2016 | Reilly |
| 9,555,379 B2 | 1/2017 | Schriver et al. |
| 9,901,671 B2 | 2/2018 | Toews et al. |
| 9,987,413 B2 | 6/2018 | Seibold et al. |
| 10,041,483 B2 | 8/2018 | Chappel et al. |
| 10,112,008 B2 | 10/2018 | Neftel et al. |
| 10,201,666 B2 | 2/2019 | Cowan et al. |
| 10,391,234 B2 | 8/2019 | Sams et al. |
| 10,549,084 B2 | 2/2020 | Sokolov et al. |
| 10,583,256 B2 | 3/2020 | Berry et al. |
| 2001/0018937 A1 | 9/2001 | Nemoto |
| 2001/0027265 A1 | 10/2001 | Prince |
| 2001/0056233 A1 | 12/2001 | Uber et al. |
| 2002/0007116 A1 | 1/2002 | Zatezalo et al. |
| 2002/0010551 A1 | 1/2002 | Wang et al. |
| 2002/0026148 A1 | 2/2002 | Uber et al. |
| 2002/0099254 A1 | 7/2002 | Movahed |
| 2002/0123702 A1 | 9/2002 | Cho |
| 2002/0151854 A1 | 10/2002 | Duchon et al. |
| 2003/0050556 A1 | 3/2003 | Uber et al. |
| 2003/0120171 A1 | 6/2003 | Diamantopoulos et al. |
| 2003/0195462 A1 | 10/2003 | Mann et al. |
| 2003/0212364 A1 | 11/2003 | Mann et al. |
| 2003/0216683 A1 | 11/2003 | Shekalim |
| 2003/0226539 A1 | 12/2003 | Kim et al. |
| 2004/0011740 A1 | 1/2004 | Bernard et al. |
| 2004/0025452 A1 | 2/2004 | Mclean |

(56) References Cited

U.S. PATENT DOCUMENTS

| | | |
|---|---|---|
| 2004/0044302 A1 | 3/2004 | Bernard et al. |
| 2004/0064041 A1 | 4/2004 | Lazzaro et al. |
| 2004/0092905 A1 | 5/2004 | Azzolini |
| 2004/0097806 A1 | 5/2004 | Hunter et al. |
| 2004/0154788 A1 | 8/2004 | Symonds |
| 2004/0162484 A1 | 8/2004 | Nemoto |
| 2004/0163655 A1 | 8/2004 | Gelfand et al. |
| 2004/0167415 A1 | 8/2004 | Gelfand et al. |
| 2004/0215144 A1 | 10/2004 | Duchon et al. |
| 2004/0253183 A1 | 12/2004 | Uber, III et al. |
| 2004/0254533 A1 | 12/2004 | Schriver et al. |
| 2005/0107697 A1 | 5/2005 | Berke et al. |
| 2005/0171487 A1 | 8/2005 | Haury et al. |
| 2005/0234407 A1 | 10/2005 | Spohn et al. |
| 2005/0234428 A1 | 10/2005 | Spohn et al. |
| 2006/0052794 A1 | 3/2006 | Mcgill et al. |
| 2006/0079765 A1 | 4/2006 | Neer et al. |
| 2006/0079843 A1* | 4/2006 | Brooks ............. A61M 5/14546 600/432 |
| 2006/0167415 A1 | 7/2006 | Nemoto |
| 2007/0068964 A1 | 3/2007 | Tanaami et al. |
| 2007/0129705 A1 | 6/2007 | Trombley et al. |
| 2007/0161970 A1 | 7/2007 | Spohn et al. |
| 2007/0219496 A1 | 9/2007 | Kamen et al. |
| 2007/0276327 A1 | 11/2007 | Kalafut et al. |
| 2008/0015406 A1 | 1/2008 | Dlugos et al. |
| 2008/0045925 A1 | 2/2008 | Stepovich et al. |
| 2008/0086087 A1 | 4/2008 | Spohn et al. |
| 2008/0167621 A1 | 7/2008 | Wagner et al. |
| 2008/0183131 A1 | 7/2008 | Duchon et al. |
| 2009/0112164 A1 | 4/2009 | Reilly et al. |
| 2009/0216192 A1 | 8/2009 | Schriver et al. |
| 2009/0234226 A1 | 9/2009 | Nemoto |
| 2009/0247865 A1 | 10/2009 | Spohn et al. |
| 2009/0247961 A1 | 10/2009 | Carlyon |
| 2009/0312744 A1 | 12/2009 | Keeley et al. |
| 2010/0130809 A1 | 5/2010 | Morello |
| 2010/0222768 A1 | 9/2010 | Spohn et al. |
| 2010/0249586 A1 | 9/2010 | Cocker et al. |
| 2010/0262078 A1 | 10/2010 | Blomquist |
| 2010/0331779 A1 | 12/2010 | Nystrom et al. |
| 2011/0275988 A1 | 11/2011 | Davis et al. |
| 2012/0089114 A1 | 4/2012 | Hemond et al. |
| 2012/0101472 A1 | 4/2012 | Schroeder et al. |
| 2012/0123229 A1 | 5/2012 | Butterfield et al. |
| 2012/0123257 A1* | 5/2012 | Stokes, Jr. .......... A61M 5/1782 600/432 |
| 2012/0178629 A1 | 7/2012 | Hudson et al. |
| 2012/0203177 A1 | 8/2012 | Lanier, Jr. et al. |
| 2012/0204997 A1 | 8/2012 | Winn et al. |
| 2012/0217231 A1 | 8/2012 | Moore et al. |
| 2012/0245560 A1 | 9/2012 | Hochman |
| 2013/0030290 A1* | 1/2013 | Nemoto ............. A61M 5/16827 600/432 |
| 2013/0123619 A1* | 5/2013 | Griggs ...................... G01L 7/00 600/432 |
| 2013/0245439 A1 | 9/2013 | Small et al. |
| 2013/0245604 A1 | 9/2013 | Kouyoumjian et al. |
| 2013/0261993 A1 | 10/2013 | Ruchti et al. |
| 2014/0027009 A1 | 1/2014 | Riley et al. |
| 2014/0142537 A1 | 5/2014 | Gibson et al. |
| 2014/0276550 A1 | 9/2014 | Uram et al. |
| 2016/0030662 A1 | 2/2016 | Uber, III et al. |
| 2016/0278725 A1 | 9/2016 | Van Nijnatten |
| 2016/0331896 A1 | 11/2016 | Nemoto et al. |
| 2017/0035974 A1 | 2/2017 | Berry et al. |
| 2017/0056603 A1 | 3/2017 | Cowan et al. |
| 2017/0143898 A1 | 5/2017 | Grosse-Wentrup et al. |
| 2017/0258982 A1 | 9/2017 | Kemper |
| 2017/0290971 A1 | 10/2017 | Hedmann et al. |
| 2017/0343446 A1 | 11/2017 | Ciolkosz et al. |
| 2018/0133392 A1 | 5/2018 | Dembo et al. |
| 2019/0083699 A1 | 3/2019 | Spohn et al. |

FOREIGN PATENT DOCUMENTS

| | | |
|---|---|---|
| CA | 2234050 A1 | 4/1997 |
| CN | 1671428 A | 9/2005 |
| CN | 103347552 A | 10/2013 |
| DE | 3203594 A1 | 8/1983 |
| DE | 3726452 A1 | 2/1989 |
| DE | 4426387 A1 | 8/1995 |
| DE | 19702896 A1 | 7/1997 |
| DE | 19647701 A1 | 5/1998 |
| DE | 19919572 A1 | 11/2000 |
| EP | 0121216 A1 | 10/1984 |
| EP | 0129910 A1 | 1/1985 |
| EP | 0189491 A1 | 8/1986 |
| EP | 0192786 A2 | 9/1986 |
| EP | 0245160 A1 | 11/1987 |
| EP | 0319275 A1 | 6/1989 |
| EP | 0337924 A2 | 10/1989 |
| EP | 0343501 A2 | 11/1989 |
| EP | 0364966 A1 | 4/1990 |
| EP | 0365301 A1 | 4/1990 |
| EP | 0372152 A1 | 6/1990 |
| EP | 0378896 A2 | 7/1990 |
| EP | 0429191 A2 | 5/1991 |
| EP | 0471455 A2 | 2/1992 |
| EP | 0475563 A1 | 3/1992 |
| EP | 0595474 A2 | 5/1994 |
| EP | 0600448 A2 | 6/1994 |
| EP | 0619122 A1 | 10/1994 |
| EP | 0439711 B1 | 5/1995 |
| EP | 0869738 A1 | 10/1998 |
| EP | 1016427 A2 | 7/2000 |
| EP | 2990073 A1 | 3/2016 |
| FR | 2493708 A1 | 5/1982 |
| FR | 2561949 A1 | 10/1985 |
| GB | 201800 A | 8/1923 |
| GB | 2252656 A | 8/1992 |
| GB | 2328745 A | 3/1999 |
| JP | S5017781 A | 2/1975 |
| JP | S5815842 A | 1/1983 |
| JP | S59214432 A | 12/1984 |
| JP | S60194934 A | 10/1985 |
| JP | S60194935 A | 10/1985 |
| JP | S60253197 A | 12/1985 |
| JP | S62216199 A | 9/1987 |
| JP | S6340538 A | 2/1988 |
| JP | S63290547 A | 11/1988 |
| JP | H01207038 A | 8/1989 |
| JP | H02224647 A | 9/1990 |
| JP | H02234747 A | 9/1990 |
| JP | H0355040 A | 3/1991 |
| JP | H04115677 A | 4/1992 |
| JP | H0584296 A | 4/1993 |
| JP | H07178169 A | 7/1995 |
| JP | H0849598 A | 2/1996 |
| JP | H0999034 A | 4/1997 |
| JP | H10211198 A | 8/1998 |
| JP | 2000175900 A | 6/2000 |
| JP | 2003102724 A | 4/2003 |
| JP | 2003116843 A | 4/2003 |
| JP | 2003210456 A | 7/2003 |
| JP | 2003225234 A | 8/2003 |
| JP | 2004174008 A | 6/2004 |
| JP | 2004236849 A | 8/2004 |
| JP | 2004298550 A | 10/2004 |
| JP | 4960180 B2 | 6/2012 |
| JP | 5063593 B2 | 10/2012 |
| JP | 5203971 B2 | 6/2013 |
| JP | 5227791 B2 | 7/2013 |
| JP | 5490840 B2 | 5/2014 |
| WO | 8001754 A1 | 9/1980 |
| WO | 8500292 A1 | 1/1985 |
| WO | 8803815 A1 | 6/1988 |
| WO | 9114232 A1 | 9/1991 |
| WO | 9114233 A1 | 9/1991 |
| WO | 9315658 A1 | 8/1993 |
| WO | 9325141 A1 | 12/1993 |
| WO | 9415664 A1 | 7/1994 |
| WO | 9632975 A1 | 10/1996 |

(56) References Cited

FOREIGN PATENT DOCUMENTS

| | | |
|---|---|---|
| WO | 9712550 A1 | 4/1997 |
| WO | 9820919 A1 | 5/1998 |
| WO | 9924095 A2 | 5/1999 |
| WO | 0061216 A1 | 10/2000 |
| WO | 0141835 A2 | 6/2001 |
| WO | 03015633 A1 | 2/2003 |
| WO | 2004012787 A2 | 2/2004 |
| WO | 2004035116 A1 | 4/2004 |
| WO | 2004091688 A2 | 10/2004 |
| WO | 2005016165 A1 | 2/2005 |
| WO | 2005035995 A1 | 4/2005 |
| WO | 2006042093 A1 | 4/2006 |
| WO | 2007079016 A2 | 7/2007 |
| WO | 2007092618 A2 | 8/2007 |
| WO | 2007116840 A1 | 10/2007 |
| WO | 2007116862 A1 | 10/2007 |
| WO | 2007116891 A1 | 10/2007 |
| WO | 2007133942 A2 | 11/2007 |
| WO | 2008078604 A1 | 7/2008 |
| WO | 2008106108 A1 | 9/2008 |
| WO | 2009051995 A1 | 4/2009 |
| WO | 2010027636 A1 | 3/2010 |
| WO | 2010117841 A1 | 10/2010 |
| WO | 2011002744 A1 | 1/2011 |
| WO | 2011097487 A2 | 8/2011 |
| WO | 2011125303 A1 | 10/2011 |
| WO | 2012048277 A2 | 4/2012 |
| WO | 2012155035 A1 | 11/2012 |
| WO | 2013043868 A1 | 3/2013 |
| WO | 2014144651 A2 | 9/2014 |
| WO | 2014179326 A1 | 11/2014 |
| WO | 2014190264 A1 | 11/2014 |
| WO | 2015106107 A1 | 7/2015 |
| WO | 2015164783 A1 | 10/2015 |
| WO | 2016112163 A1 | 7/2016 |
| WO | 2016172467 A1 | 10/2016 |
| WO | 2016191485 A1 | 12/2016 |
| WO | 2017012781 A1 | 1/2017 |
| WO | 2017038575 A1 | 3/2017 |
| WO | 2017096072 A1 | 6/2017 |
| WO | 2017152036 A1 | 9/2017 |
| WO | 2018060505 A1 | 4/2018 |
| WO | 2018075386 A1 | 4/2018 |
| WO | 2018089882 A1 | 5/2018 |

OTHER PUBLICATIONS

Angelini, P., "Use of mechanical injectors during percutaneous transluminal coronary angioplasty (PTCA)," Catheterization and Cardiovascular Diagnosis, vol. 16, Issue 3, pp. 193-194, Mar. 1989.

Awai, K., et al., "Effect of contrast material injection duration and rate on aortic peak time and peak enhancement at dynamic CT involving injection protocol with dose tailored to patient weight," Radiology, vol. 230, Issue 1, pp. 142-150, 2004.

Bae, et al. "Aortic and Hepatic Contrast Medium Enhancement at CT—Part I, Prediction with a Computer Model", Radiology 1998;207:647-655.

Bae, K.T., et al., "Multiphasic Injection Method for Uniform Prolonged Vascular Enhancement at CT Angiography Pharmacokinetic Analysis and Experimental Porcine Model," Radiology, vol. 216, Issue 3, pp. 872-880 (Sep. 2000).

Bae, K.T. et al, "Peak Contrast Enhancement in CT and MR Angiography: When Does it Occur and Why? Pharmacokinetic Study in a Porcine Model", Radiology, vol. 227, Jun. 2003, pp. 809-816.

Bae, K.T., et al., "Uniform vascular contrast enhancement and reduced contrast medium vol. achieved by using exponentially decelerated contrast material injection method," Radiology, vol. 231, Issue 3, pp. 732-736, 2004.

Baker, Aaron; et al. "Fluid Mechanics Analysis of a Spring-Loaded Jet Injector." IEEE Transactions on Biomedical Engineering, vol. 46, No. 2, Feb. 1999.

Becker, C.R., et al., "Optimal contrast application for cardiac 4-detector-row computed tomography," Investigative Radiology, vol. 38, Issue 11, pp. 690-694 (Nov. 2003).

Blomley, M.J.K. and Dawson, P., "Bolus Dynamics: Theoretical and Experimental Aspects," The Brit. J. ofRadiology, vol. 70, No. 832, pp. 351-359 (Apr. 1997).

Brunette J.; et al., "Comparative rheology of low- and iso-osmolarity contrast agents at different temperature", Catheterization and Cardiovascular Interventions, 2008, vol. 71 Issue No. 1, 78-83.

Cademartiri, F. and Luccichenti, G., et al. "Sixteen-row multislice computed tomography: basic concepts, protocols, and enhanced clinical applications," Seminars in Ultrasound, CT and MRI, vol. 25, Issue 1, pp. 2-16, 2004.

Dardik, H. et al., "Remote Hydraulic Syringe Actuator," Arch. Surg., vol. 115, Issue 1, Jan. 1980.

Dawson, P. and Blomley, M., "The value of mathematical modelling in understanding contrast enhancement in CT with particular reference to the detection of hypovascular liver metastases," European Journal of Radiology, vol. 41, Issue 3, pp. 222-236 (Mar. 2002).

"Digital Injector for Angiography", Sias. (Sep. 7, 1993).

Disposable Low-Cost Catheter Tip Sensor Measures Blood Pressure during Surgery, Sensor (Jul. 1989).

EZ Chem Brochure, E-Z-EM, Inc. (Jul. 2007).

Fisher, M.E. and Teo, K.L., "Optimal insulin infusion resulting from a mathematical model of blood glucose dynamics", IEEE Transactions on Biomedical Engineering, vol. 36, Issue 4, pp. 479-486, 1989.

Flegal, K.M., et al., "Prevalence and trends in obesity among US adults," JAMA, 2002, vol. 288, Issue 14, pp. 1-4, (1999-2000).

Fleischmann, D. and Hittmair, K., "Mathematical analysis of arterial enhancement and optimization of bolus geometry for CT angiography using the discrete Fourier transform," Journal of Computer Assisted Tomography, vol. 23, Issue 3, pp. 474-484 (May/Jun. 1999).

Fleischmann, D., "Contrast Medium Injection Technique," In: U. Joseph Schoepf: "Multidetector—Row CT of the Thorax," pp. 47-59 (Jan. 22, 2004).

Fleischmann, D., "Present and Future Trends in Multiple Detector—Row CT Applications; CT Angiography", European Radiology, vol. 12, Issue 2, Supplement 2, Jul. 2002, pp. s11-s15.

Gardiner, G. A., et al., "Selective Coronary Angiography Using a Power Injector," AJR Am J Roentgenol., vol. 146, Issue 4, pp. 831-833 (Apr. 1986).

Garrett, J. S., et al., "Measurement of cardiac output by cine computed tomography," The American Journal of Cardiology, vol. 56, Issue 10, pp. 657-661, 1985.

Gembicki, F.W., "Vector Optimization for Control with Performance and Parameter Sensitivity Indices," PhD Thesis Case Western Reserve University, 1974.

Gentilini A., et al., "A new paradigm for the closed-loop intraoperative administration of analgesics in humans," IEEE Transactions on Biomedical Engineering, vol. 49, Issue 4, pp. 289-299 (Apr. 2002).

Gerlowski L.E. and Jain R.K., "Physiologically Based Pharmacokinetic Modeling: Principles and Applications," Journal of Pharmaceutical Sciences, vol. 72, pp. 1104-1125, Oct. 1983.

Goss, J. E., et al., "Power injection of contrast media during percutaneous transluminal coronary artery angioplasty," Catheterization and Cardiovascular Diagnosis, vol. 16, Issue 3, pp. 195-198 (Mar. 1989).

Grant, S.C.D. et al., "Reduction of Radiation Exposure to the Cardiologist during Coronary Angiography by the Use of a Remotely Controlled Mechanical Pump for Injection of Contrast Medium," Catheterization and Cardiovascular Diagnosis, vol. 25, Issue 2, pp. 107-109 (Feb. 1992).

Hackstein, N. et al., "Glomerular Filtration Rate Measured by Using Triphasic Helical CT with a Two-Point Patlak Plot Technique," Radiology, vol. 230, Issue 1, pp. 221-226, Jan. 2004.

Hansen, P.C, Regularization tools: a MATLAB package for analysis and solution of discrete ill-posed problems, Numerical Algorithms, vol. 6, Issue 1, pp. 35, 1994.

Hansen, P.C., "The truncated SVD as a method for regularization," BIT Numerical Mathematics, vol. 27, Issue 4, pp. 534-555, 1987.

(56) References Cited

OTHER PUBLICATIONS

Harris P., H. D. "The Human Pulmonary Circulation," Edinburgh, Churchill Livingstone, (Appendix I), 1986.
Hayes, M., "Statistical Digital Signal Processing and Modeling", New York, New York, Wiley and Sons, 1996, pp. 154-177, (Prony's method).
Heiken; J.P. et al., "Dynamic Contrast-Enhanced CT of the Liver: Comparison of Contrast Medium Injection Rates and Uniphasicand Biphasic Injection Protocols", Radiology, May 1993, vol. 187, No. 2, pp. 327-331.
"Infus O.R. Multi-Drug Syringe Pump with Smart Labels," Bard MedSystems Division Inc., pp. 2693-2696 (2005).
"International Preliminary Report on Patentability from PCT Application No. PCT/US2018/048283", dated Mar. 12, 2020.
Ireland, M.A., et al., "Safety and Convenience of a Mechanical Injector Pump for Coronary Angiography,"Catheterization and Cardiovascular Diagnosis, vol. 16, Issue 3, pp. 199-201 (1989).
Jacobs, J.R, "Algorithm for optimal linear model-based control with application to pharmacokinetic model-driven drug delivery," IEEE Transactions on Biomedical Engineering, vol. 37, Issue 1, pp. 107-109 (Jan. 1990).
Korosec, F.R., "Physical Principles of Phase-Contrast, Time-of-Flight, and Contrast-Enhanced MR Angiography," 41st Annual Meeting of American Association of Physicists in Medicine, Jul. 25-29, 1999.
Korosec, Frank, "Basic Principles of Phase-contrast, Time-of-flight, and Contrast-enhanced MR Angiography", 1999.
Krause, W, "Application of pharmacokinetics to computed tomography: injection rates and schemes: mono-, bi-, or multiphasic?," Investigative Radiology, vol. 31, Issue 2, pp. 91-100, Feb. 1996.
Krieger, R. A., "CO2-Power-Assisted Hand-Held Syringe: Better Visualization during Diagnostic and InterventionalAngiography," Cathet Cardiovasc Diagn., vol. 19, Issue 2, pp. 123-128 (Feb. 1990).
Liebel-Flarsheim Company, "Angiomat 6000 Digital Injection System—Operator's Manual", Document No. 600950, Rev. 1, Jan. 1990.
Mahnken, A. H., et al., "Determination of cardiac output with multislice spiral computed tomography: a validation study," Investigative Radiology, vol. 39, Issue 8, pp. 451-454, Aug. 2004.
Mahnken, A. H., et al., "Measurement of cardiac output from a test-bolus injection in multislice computed tomography," European Radiology, vol. 13, Issue 11, pp. 2498-2504, 2003.
Mark V/Mark V Plus Injector Operation Manual KMP 805P Rev. B. Medrad, Inc, 1990.
Mcclellan, J.H., "Parametric Signal Modeling," Chapter 1 in Advanced Topics in Signal Processing, Pentice-Hall, Englewood Cliffs, NJ (1988).
MCT and MCT Plus Injection Systems Operation Manual KMP 810P, Medrad, Inc, 1991.
Morden Peter.; et al., "The Role of Saline Flush Injection Rate in Displacement of CT Injectable Peripherally Inserted Central Catheter Tip During Power Injection of Contrast Material", AJR, Jan. 2014, 202, W13-W18.
Neatpisarnvanit, C. and Boston, J.R., "Estimation of plasma insulin from plasma glucose", IEEE Transactions on Biomedical Engineering, vol. 49, Issue 11, pp. 1253-1259, 2002.
Ostergaard, L., et al., "High resolution measurement of cerebral blood flow using intravascular tracer boluspassages. Part 1: Mathematical approach and statistical analysis," Magnetic Resonance in Medicine, vol. 36, Issue 5,pp. 715-725 (Nov. 1996).
Ostergaard, L., et al., "High resolution measurement of cerebral blood flow using intravascular tracer boluspassages. Part II: Experimental comparison and preliminary results," Magn Reson Med, vol. 36, Issue 5, pp. 726-736(Nov. 1996).
Parker, K.J., et al., "A Particulate Contrast Agent With Potential for Ultrasound Imaging of Liver," Ultrasound in Medicine & Biology, vol. 13, Issue 9, pp. 555-566 (Sep. 1987).
Rosen, B.R. et al., "Perfusion Imaging with NMR Contrast Agents," Magentic Resonance in Medicine, vol. 14, No. 2, pp. 249-265, May 1, 1990.
Sablayrolles, J-L, "Cardiac CT: Experience from Daily Practice", Advance CT, A GE Healthcare Publication. Aug. 2004.
Stevens, M.A., et al. "A Prospective Randomized Trial of Prevention Measures in Patients at High Risk for Contrast Nephropathy," J. of the ACC, vol. 33, Issue 2, pp. 403-411, Feb. 1999.
"The Solution for Your IV Formulas", Valley Lab. Inc., E-39-15, 3399, 3400, 2646.
Wada D.R. and Ward; D.S., "The hybrid model: a new pharmacokinetic model for computer-controlled infusion pumps", IEEE Transactions on Biomedical Engineering, 1994, vol. 41, Issue 2, pp. 134-142.
Wada, D.R. and Ward, D.S., "Open loop control of multiple drug effects in anesthesia", IEEE Transactions on Biomedical Engineering, vol. 42, Issue 7, pp. 666-677, 1995.
Yamashita, Y. et al., "Abdominal Helical CT: Evaluation of Optimal Doses of Intravenous Contrast Material—A Prospective Randomized Study," Radiology, vol. 216, Issue 3, pp. 718-723, Sep. 1, 2000.
Angiography, Catheterization and Cardiovascular Diagnosis, vol. 19, pp. 123-128, 1990.
Awai Kazuo; et al, "Aortic and Hepatic Enhancement and Tumor-to-Liver Contrast Analysis of the Effect of Different Concentrations of Contrast Material at Multi-Detector Row Helical CT.", Radiology, 2002, vol. 224; Issue 3., 757-763.

* cited by examiner

METHOD FOR DYNAMIC PRESSURE CONTROL IN A FLUID INJECTOR SYSTEM

CROSS REFERENCE TO RELATED APPLICATIONS

This application is a U.S. national phase application under 35 U.S.C. § 371 of PCT International Application No. PCT/US2018/048283, filed 28 Aug. 2018 and claims priority to U.S. Provisional Application No. 62/552,433, titled "System and Method for Dynamic Pressure Equalization in a Fluid Injector System" and filed on 31 Aug. 2017, the disclosures of which are incorporated herein in their entirety.

BACKGROUND OF THE DISCLOSURE

Field of the Disclosure

The present disclosure relates generally to fluid delivery systems and methods, and, in particular, to a system and method for performing an injection using a fluid delivery system with dynamic pressure control of two or more fluids during an injection protocol.

Description of Related Art

In many medical diagnostic and therapeutic procedures, a medical practitioner, such as a physician, injects a patient with one or more medical fluids. In recent years, a number of fluid delivery systems having injector-actuated syringes and fluid injectors for pressurized injection of fluids, such as a contrast solution (often referred to simply as "contrast"), a flushing agent, such as saline, and other medical fluids have been developed for use in procedures such as angiography, computed tomography (CT), ultrasound, magnetic resonance imaging (MRI), positron emission tomography (PET), and other imaging procedures. In general, these fluid delivery systems are designed to deliver a preset amount of fluid at a desired flow rate. Typically, for a multiphase injection, fluid is delivered in a contrast phase followed by a saline flush phase. The contrast fluid provides enhancement to diagnostic images and the saline phase increases contrast flux and provides a sharp distinction with the contrast.

Differences between desired flow rate and fluid volume may be especially apparent for multiphase injections, in which two or more fluids are delivered from two or more syringes which are independently driven by a drive member of a fluid injector in a sequential fashion. Therefore, when performing a multiphase injection, it is important to consider the manner in which the fluid for the two phases is contained. If the fluid reservoirs or syringes are connected in an open system then the pressure in the two fluid locations is expected to be roughly the same during an injection due to fluid communication between the two or more syringes. However, in an open system containing two reservoirs or syringes, development of pressure in the reservoir or syringe containing the first fluid may result in fluid movement from the first reservoir to the second reservoir or syringe depending on the system compliance. This may result in unintended mixing. Such mixing may be permissible for single patient systems; however, cross contamination of the fluid reservoirs may be unacceptable for multi-patient devices.

To isolate the multiple fluid reservoirs and prevent mixing, fluid delivery systems can be constructed using a valve, such as a check valve, stopcock, or fluid manifold, to isolate respective fluid reservoirs and/or syringes. Isolating the fluid reservoirs prevents passive cross contamination of the fluid reservoirs. However, isolating fluid reservoirs can reduce or cause fluctuations in actual flow rate through a fluid delivery system in the absence of any correction or compensation. For example, actual fluid flow rates may be reduced because the second or saline fluid must be driven through the system with enough pressure to drive the first phase and to remove any slack introduced into the system during the first phase of the injection.

Accordingly, there is a need in the art for improved methods and systems for monitoring and controlling fluid flow rate through a fluid delivery system including multiple syringes or fluid reservoirs. For example, such systems may address problems of controlling flow rate through the system and preventing cross contamination of fluids contained in different syringes or reservoirs. The systems and methods disclosed herein are adapted to address such issues.

SUMMARY OF DISCLOSURE

Various examples of the present disclosure describe methods and fluid injector systems including dynamic pressure control, including pressure control or equalization between fluid in two or more reservoirs, in a fluid delivery system during a multiphase/multi-fluid injection includes providing a multiphase fluid delivery system having at least a first fluid reservoir configured for containing a first fluid, at least a second fluid reservoir configured for containing a second fluid, a fluid conduit for conducting fluid from the first reservoir and the second reservoir to a patient, and an injector having at least a first drive member for expelling fluid from the first reservoir and at least a second drive member for expelling fluid from the second reservoir.

Various embodiments of the present disclosure provide methods for dynamic pressure and fluid flow control. In certain embodiments, the method comprises advancing the first drive member to expel the first fluid from the first reservoir into the conduit during a first injection phase, wherein the first fluid is pressurized to a first fluid pressure. The method then includes measuring the first fluid pressure during the first injection phase to provide a target value, wherein the target value is based at least on the measured fluid pressure of the first fluid phase. After the target value is determined and while the second reservoir is in fluid isolation from the conduit, the method includes advancing or retracting the second drive member to increase or decrease the fluid pressure of the second fluid in the second reservoir to the target value. The first reservoir and the second reservoir may be placed in fluid isolation from the conduit by closing a valve, such as a stopcock, pinch valve, high pressure crack valve, etc. The method then includes placing the second reservoir in fluid communication with the conduit and advancing the second drive member to expel the second fluid from the second reservoir into the conduit at a pressure equal to the target value.

According to various embodiments, the target value may be substantially equal to the first fluid pressure. In other embodiments, the target value may be greater than the first fluid pressure. In other embodiments, the target value may be less than the first fluid pressure. The target value may be determined by a processor associated with the fluid injector based on the specific fluid injection parameters and protocol, for example by calculation of the target value based on various factors, such as desired flow rates of the first fluid and second fluid, fluid types (e.g., contrast versus saline), system capacitance, whether dual flow injection is desired, whether backflow may be an issue, among other factors.

In certain embodiments, the step of advancing the second drive member to expel the second fluid from the second reservoir may further comprise continuing to advance the first drive member to expel the first fluid from the first reservoir to provide a dual flow fluid delivery of a predetermined ratio of the first fluid and the second fluid. The predetermined ratio may be a specified ratio ranging from 1:99 of the first fluid to the second fluid to 99:1 of the first fluid to the second fluid that may be pre-programmed into the processor by a user for a certain injection protocol.

In other embodiments, the method may further comprise isolating the first reservoir from fluid communication with the conduit prior to placing the second fluid reservoir in fluid communication with the conduit or, alternatively, prior to advancing the second drive member to expel the second fluid from the second reservoir in to the conduit. According to these embodiments, the injection protocol may include transitioning the injection from the first fluid to the second fluid while avoiding fluctuations in fluid flow during the transition, for example when there is a difference in viscosity between the first fluid and the second fluid (such as a contrast media which can range from 2.0 to 30.0 cP (at 20° C.), to a lower viscosity fluid, such as saline having a viscosity of 1.0 to 1.5 cP (at 20° C.)), or avoiding backflow of the second fluid into the first fluid reservoir, or vice versa. In various embodiments, the first fluid may be a contrast imaging agent, such as a CT contrast, a CV contrast, an MR contrast, or a PET contrast; and the second fluid may be a flushing fluid, such as saline, Ringer's lactate, water, etc. Alternatively, the first fluid may be a flushing agent and the second fluid may be a contrast, as described herein.

According to other embodiments, the fluid injector may further comprise at least a third fluid reservoir in selectable fluid communication with the conduit and operatively engaged with at least a third drive member of the fluid injector for expelling at least a third fluid into the conduit. The third fluid may be the same or different that the first fluid and/or the second fluid.

In other embodiments, the present disclosure provides a fluid delivery system configured for dynamic pressure control during a multiphase/multi-fluid injection, where the fluid delivery system comprises: at least a first reservoir configured for containing a first fluid; at least a second reservoir configured for containing a second fluid; a conduit connected to the first reservoir and the second reservoir for conducting fluid from the reservoirs to a patient; a fluid injector having at least a first drive member for expelling fluid from the first reservoir and at least a second drive member for expelling fluid from the second reservoir; and a controller in electronic communication with the fluid injector including computer readable memory. The controller may be associated with the fluid injector, a stand-alone operating computer, a removable operating storage media, a hospital information network, or outside computer. The memory includes instructions that when executed by the controller cause the controller to: instruct the injector to advance the first drive member to expel the first fluid from the first reservoir during a first injection phase, wherein the first fluid is pressurized to a first fluid pressure; measure the first fluid pressure during the first injection phase to provide a target value, wherein the target value is based on the measured fluid pressure of the first fluid phase; while the second reservoir is in fluid isolation from the conduit, instruct the injector to advance the second drive member to increase the fluid pressure of the second fluid in the second reservoir to the target value; instruct the injector to place the second reservoir in fluid communication with the conduit; and instruct the injector to advance the second drive member to expel the second fluid from the second reservoir into the conduit at a pressure equal to the target value. The fluid delivery system may be programmed to or optionally generate and display a notification instructing the user to establish fluid communication between the second reservoir and the conduit. Other programmed instructions within the processor are described herein.

Clause 1. A method for dynamic pressure control in a fluid delivery system during a multiphase/multi-fluid injection, comprising: providing a multiphase fluid delivery system comprising at least a first fluid reservoir configured for containing a first fluid, at least a second fluid reservoir configured for containing a second fluid, a fluid conduit for conducting the first fluid from the first reservoir and the second fluid from the second reservoir to a patient, and an injector comprising at least a first drive member for expelling the first fluid from the first reservoir and at least a second drive member for expelling the second fluid from the second reservoir; advancing the first drive member to expel the first fluid from the first reservoir into the conduit during a first injection phase, wherein the first fluid is pressurized to a first fluid pressure; measuring the first fluid pressure during the first injection phase to provide a target value, wherein the target value is based on the measured fluid pressure of the first fluid phase; while the second reservoir is in fluid isolation from the conduit, advancing or retracting the second drive member to increase or decrease the fluid pressure of the second fluid in the second reservoir to the target value; placing the second reservoir in fluid communication with the conduit; and advancing the second drive member to expel the second fluid from the second reservoir into the conduit at a pressure equal to the target value. The second drive member may be advanced to expel the second fluid from the second reservoir to provide a pressure equal to a target value for at least the initial portion of the second fluid.

Clause 2. The method of clause 1, further comprising isolating the first reservoir from fluid communication with the conduit prior to advancing the second drive member to expel the second fluid from the second reservoir into the conduit.

Clause 3. The method of clause 1 or 2, wherein the target value is substantially equal to the first fluid pressure.

Clause 4. The method of clause 1 or 2, wherein the target value is greater than the first fluid pressure.

Clause 5. The method of clause 1 or 2, wherein the target value is less than the first fluid pressure.

Clause 6. The method of any one of clauses 1 to 5, wherein advancing the second drive member further comprises continuing to advance the first drive member to expel the first fluid from the first reservoir to provide a dual flow fluid delivery of a predetermined ratio of the first fluid and the second fluid.

Clause 7. The method of clause 6, further comprising adjusting the first fluid pressure and the second fluid pressure to provide the dual flow fluid delivery, wherein the predetermined ratio is a specified ratio ranging from 1:99 of the first fluid to the second fluid to 99:1 of the first fluid to the second fluid.

Clause 8. The method of any one of clauses 1 to 7, wherein the first fluid comprises an imaging contrast media and the second fluid comprises saline.

Clause 9. The method of any one of clauses 1 to 8, wherein the first fluid reservoir and the at least the second fluid reservoir are fluid reservoirs independently selected from the group consisting of a syringe, a peristaltic pump, and a compressible bag.

Clause 10. The method of any one of clauses 1 to 9, wherein at least one of the first fluid reservoir and the at least the second fluid reservoir is a syringe.

Clause 11. The method of any one of clauses 1 to 10, wherein the first fluid reservoir and the at least the second fluid reservoir are syringes.

Clause 12. The method of any one of clauses 1 to 11, further comprising at least one third fluid reservoir in selectable fluid communication with the conduit and operatively engaged with at least one third drive member of the fluid injector for expelling at least a third fluid into the conduit.

Clause 13. The method of any one of clauses 1 to 12, wherein each fluid reservoir is independently in selective fluid communication with the conduit by a respective valve.

Clause 14. The method of clause 13, wherein each of the respective valves comprises a first, fill position wherein the fluid reservoir is in fluid communication with a fluid container but in fluid isolation with the conduit, a second, closed position wherein the fluid reservoir is in fluid isolation with the respective fluid container and the conduit, and a third, delivery position where the fluid reservoir is in fluid communication with the conduit but in fluid isolation with the fluid container.

Clause 15. The method of clause 13 or 14, wherein each of the respective valves is operatively controlled by a processor of the fluid injector.

Clause 16. A fluid delivery system configured for dynamic pressure control during a multiphase/multi-fluid injection, comprising: at least a first reservoir configured for containing a first fluid; at least a second reservoir configured for containing a second fluid; a conduit connected to the first reservoir and the second reservoir for conducting fluid from the first and second reservoirs to a patient; a fluid injector comprising at least a first drive member for expelling the first fluid from the first reservoir and at least a second drive member for expelling the second fluid from the second reservoir; and a controller in electronic communication with the fluid injector comprising computer readable memory containing instructions that, when executed by the controller, causes the controller to: instruct the injector to advance the first drive member to expel the first fluid from the first reservoir during a first injection phase, wherein the first fluid is pressurized to a first fluid pressure; measure the first fluid pressure during the first injection phase to provide a target value, wherein the target value is based on the measured fluid pressure of the first fluid phase; while the second reservoir is in fluid isolation from the conduit, instruct the injector to advance the second drive member to increase the fluid pressure of the second fluid in the second reservoir to the target value; instruct the injector to place the second reservoir in fluid communication with the conduit; and instruct the injector to advance the second drive member to expel the second fluid from the second reservoir into the conduit at a pressure equal to the target value.

Clause 17. The fluid delivery system of clause 16, wherein the controller comprises further computer readable memory containing instructions that, when executed by the controller, causes the controller to: instruct the injector to isolate the first fluid reservoir from fluid communication with the conduit prior to instructing the injector to advance the second drive member to expel the second fluid from the second reservoir into the conduit.

Clause 18. The fluid delivery system of clause 16, wherein the controller comprises further computer readable memory containing instructions that, when executed by the controller, causes the controller to: concurrent with instructing the injector to advance the second drive member to expel the second fluid, instruct the injector to continue to advance the first drive member to expel the first fluid from the first reservoir to provide a dual flow fluid delivery of a predetermined ratio of the first fluid and the second fluid.

Clause 19. The fluid delivery system of clause 18, wherein the controller comprises further computer readable memory containing instructions that, when executed by the controller, causes the controller to: during the dual flow fluid delivery, instruct the fluid injector to adjust the first fluid pressure and the second fluid pressure to provide the dual flow fluid delivery, wherein the predetermined ratio is a specified ratio ranging from 1:99 of the first fluid to the second fluid to 99:1 of the first fluid to the second fluid.

Clause 20. The fluid delivery system of any one of clauses 16 to 19, wherein the first fluid reservoir and the at least the second fluid reservoir are fluid reservoirs independently selected from the group consisting of a syringe, a peristaltic pump, and a compressible bag.

Clause 21. The fluid delivery system of any one of clauses 16 to 20, wherein at least one of the first fluid reservoir and the at least the second fluid reservoir is a syringe.

Clause 22. The fluid delivery system of any one of clauses 16 to 21, wherein the first fluid reservoir and the at least the second fluid reservoir are syringes.

Clause 23. The fluid delivery system of any one of clauses 16 to 22, wherein the fluid injector further comprises at least one third fluid reservoir in selectable fluid communication with the conduit and operatively engaged with at least one third drive member of the fluid injector for expelling at least a third fluid into the conduit.

Clause 24. The fluid delivery system of any of clauses 16 to 23, wherein each fluid reservoir is independently in selective fluid communication with the conduit by a respective valve.

Clause 25. The fluid delivery system of any of clauses 16 to 24, wherein each of the respective valves comprises a first, fill position wherein the fluid reservoir is in fluid communication with a fluid container but in fluid isolation with the conduit, a second, closed position wherein the fluid reservoir is in fluid isolation with the respective fluid container and the conduit, and a third, delivery position where the fluid reservoir is in fluid communication with the conduit but in fluid isolation with the fluid container.

Clause 26. The fluid delivery system of clause 24 or 25, wherein each of the respective valves is operatively controlled by a processor of the fluid injector.

These and other features and characteristics of a fluid delivery system and fluid injector for performing an injection with dynamic pressure control, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only.

DETAILED DESCRIPTION

Figure 1:
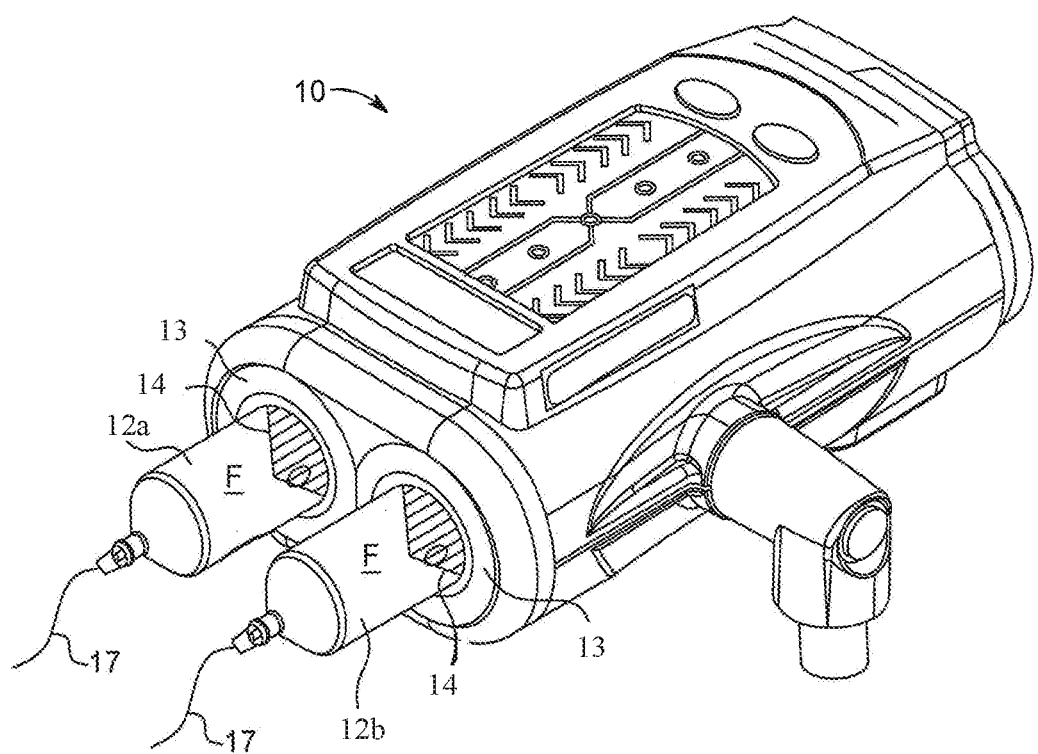
FIG. 1 is a perspective view of a fluid delivery system according to an example of the present disclosure.

As used in the specification and the claims, the singular form of "a", "an", and "the" include plural referents unless the context clearly dictates otherwise.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures.

Spatial or directional terms, such as "left", "right", "inner", "outer", "above", "below", and the like, are not to be considered as limiting as the invention can assume various alternative orientations.

All numbers used in the specification and claims are to be understood as being modified in all instances by the term "about". The term "about" means a range of plus or minus ten percent of the stated value.

Unless otherwise indicated, all ranges or ratios disclosed herein are to be understood to encompass any and all subranges or sub-ratios subsumed therein. For example, a stated range or ratio of "1 to 10" should be considered to include any and all subranges between (and inclusive of) the minimum value of 1 and the maximum value of 10; that is, all subranges or sub-ratios beginning with a minimum value of 1 or more and ending with a maximum value of 10 or less, such as but not limited to, 1 to 6.1, 3.5 to 7.8, and 5.5 to 10.

The term "at least" means "greater than or equal to".

The term "includes" is synonymous with "comprises".

When used in relation to a syringe and/or a plunger, the term "proximal" refers to a portion of a syringe and/or a plunger nearest a fluid injector when a syringe and/or a plunger is oriented for connecting to a fluid injector. The term "distal" refers to a portion of a syringe and/or a plunger farthest away from a fluid injector when a syringe and/or a plunger is oriented for connecting to a fluid injector. The term "radial" refers to a direction in a cross-sectional plane normal to a longitudinal axis of a syringe, a plunger, and/or a piston extending between proximal and distal ends. The term "circumferential" refers to a direction around an inner or outer surface of a sidewall of a syringe, a plunger, and/or a piston. The term "axial" refers to a direction along a longitudinal axis of a syringe, a piston, and/or a piston extending between the proximal and distal ends. The term "open" when used to refer to a fluid delivery component means that the system is in fluid connection with an outlet, for example through a nozzle or the open end of a tubing component or catheter. In an open system, fluid flow may be constrained, for example by forcing a fluid through a small diameter fluid path where flow may be determined by physical parameters of the system and the fluid, such as tubing diameter, fluid path constrictions, applied pressure, viscosity, etc. The term "closed" when used to refer to a fluid delivery component means that the system is not in fluid connection with an outlet, for example where fluid flow is stopped by a valve, such as a stopcock, high crack pressure valve, pinch valve, and the like. As used herein the term "slack" means mechanical slack, including a clearance or lost motion in a mechanism caused by gaps between parts, compression of mechanical components under applied load (such as by applied pressure), deflection of mechanical components under applied load (such as by applied pressure), that results in a delay of pressurized delivery of a fluid from a fluid injection after application of force.

It is to be understood that the disclosure may assume alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the examples disclosed herein are not to be considered as limiting.

Characterizing an impedance of a fluid delivery system to minimize a difference between desired and actual fluid delivery system performance requires consideration how energy from an energy source is used in or moves through the system. The energy output or loss from the fluid delivery system may be in the form of heat losses through frictional forces or of work done on the fluid delivery system. For example, some of the energy carried by the pressurized fluid as it is delivered under pressure through a catheter is lost through resistive, frictional, or dissipative heating of the fluid. Additionally, pressurized delivery of fluid can also increase the potential energy of the system in terms of an increase in overall volume of system components or compressive forces on system components, as discussed herein. Furthermore, the kinetic energy of pressurized fluid moving through the fluid delivery system can affect the overall performance of the fluid delivery system. For example, inertial forces of moving contrast material and expansion of the containers and/or tubing associated with the system may cause a phase lag between movement of the syringe plunger within the injector syringe and movement of contrast material out of the catheter and into the patient.

Due to high injection pressures, which may be on the order of 1,200 psi in some angiographic procedures, there may be an expansion of various components of the fluid delivery system, such as the syringes, tubing connected to the patient, and components of the fluid injector, such that there may be a volume of fluid in excess of the desired quantity selected for the injection procedure. Such increase in the quantity of fluid occurs due to system capacitance. Total system capacitance (also referred to as compliance or elasticity) represents the amount of fluid (i.e., excess volume) that is captured in the swelling of the components of the fluid delivery system. In general, capacitance is directly correlative to injection pressure and inversely correlative to volume of contrast medium and saline in the syringes. In other words, capacitance increases with an increase in injection pressure and an increase in pressurized volume of fluid in the syringes. Total system capacitance is inherent to each fluid delivery system and depends on a plurality of factors beyond pressure and volume of fluid remaining in the system, including, without limitation, injector construction, mechanical properties of materials used to construct the syringe, plunger, pressure jacket surrounding the syringe, fluid lines delivering the fluid to the patient, size of the syringe, plunger, pressure jacket, and fluid properties, such as temperature, viscosity, and density.

Injection rate or delivered volume can also be affected by a manner in which the syringes or reservoirs are restrained in the fluid injector. For example, tolerances are included at the interface between a disposable syringe and the injector to allow the user to connect the disposable syringe without excessive force and to prevent the disposable syringe from being damaged during attachment. While these tolerances are included for usability and manufacturing feasibility, the presence of such tolerances allows the syringe(s) to move as the drive member or the piston drives fluid through the syringe. In some cases, translation or movement of the syringe results in under delivered volume as piston motion, which causes movement of the disposable syringe does not result in delivered fluid.

Various examples of the present disclosure describe methods and fluid delivery systems comprising a fluid injector such as described herein, including dynamic pressure control, including pressure control or equalization between fluid in two or more reservoirs, in a fluid delivery system during a multiphase/multi-fluid injection includes providing a multiphase fluid delivery system having at least a first fluid reservoir configured for containing a first fluid, at least a second fluid reservoir configured for containing a second fluid, a fluid conduit for conducting fluid from the first reservoir and the second reservoir to a patient, and an injector having at least a first drive member for expelling fluid from the first reservoir and at least a second drive member for expelling fluid from the second reservoir. In various embodiments, the fluid injector system may comprise at least a third fluid reservoir in selectable fluid communication with the conduit and operatively engaged with at least one third drive member of the fluid injector for expelling at least a third fluid into the conduit. Other embodiments may further include additional fluid reservoirs.

The fluid injector and corresponding fluid reservoirs and drive members may independently be designed as a syringe (as described herein), a compressible bag with a clam-shell or other compression drive member, and a peristaltic pump with rotational drive member. For example, in certain embodiments at least one of the first fluid reservoir, the second fluid reservoir, and/or the third fluid reservoir may be a syringe, for example a front loading syringe or rolling diaphragm syringe, operatively connected to a drive member such as a piston attached to a syringe plunger or the proximal end wall of a rolling diaphragm. In specific embodiments, each of the first reservoir, the at least the second reservoir, the at least the third reservoir and any other reservoir may be a syringe operatively connected to a drive member.

According to various embodiments, each reservoir, such as the first reservoir, the at least the second reservoir, the at least the third reservoir, etc., may be independently in selective fluid communication with the conduit by a respective first valve, second valve, third valve, etc. that controls whether the system is in fluid communication or in fluid isolation with the conduit. According to certain embodiments, each of the respective valves may comprise a first, fill position wherein the fluid reservoir is in fluid communication with a fluid container but in fluid isolation with the conduit, such that proximal movement of the drive member, in the case of a syringe, draws fluid into the fluid reservoir from the fluid container. According to various embodiments, each of the respective valves may comprise a second, closed position where the fluid reservoir is fluidly isolated from at least the conduit and in specific embodiments also from the fluid container, such that the fluid reservoir is a closed system. Each of the respective valves may comprise a third, delivery position where the fluid reservoir is in fluid communication with the conduit but in fluid isolation with the fluid container, such that the fluid reservoir is an open system. Each of the respective valves may be independently controlled by the processor or controller of the fluid delivery system so that during a programmed fluid injection protocol, the valves are operated to control fluid flow of the first fluid, the second fluid, and where appropriate, the third fluid. Control of the fluid valves, in combination with advancing the corresponding drive members allows the fluid delivery system to control flow of medical fluids.

Various embodiments of the present disclosure provide methods for dynamic pressure and fluid flow control. In certain embodiments, the method comprises advancing the first drive member to expel the first fluid from the first reservoir into the conduit during a first injection phase, wherein the first fluid is pressurized to a first fluid pressure. The method then includes measuring the first fluid pressure during the first injection phase to provide a target value, wherein the target value is based at least on the measured fluid pressure of the first fluid phase. After the target value is determined and while the second reservoir is in fluid isolation from the conduit, the method includes advancing the second drive member to increase the fluid pressure of the second fluid in the second reservoir to the target value. The method then includes placing the second reservoir in fluid communication with the conduit and advancing the second drive member to expel the second fluid from the second reservoir into the conduit at a pressure equal to the target value.

According to various embodiments, the target value may be substantially equal to the first fluid pressure. As used herein, the term "substantially equal" means to within 10% of the reference value, for example from 90% to 110% of the target value. When the target value is substantially equal to the first fluid pressure, pressure equalization between the first fluid reservoir and the second fluid reservoir is obtained. In fluid injection systems that are open, i.e., no valving to isolate any of the fluid reservoirs, the fluid reservoirs are in fluid communication with each other and pressure equalization is observed, for example, pressurization of the first fluid reservoir results in pressurization of the second fluid reservoir since the fluid path provides fluid communication between the syringe reservoirs. This can have the disadvantage of a volume of the first pressurized fluid flowing into the second reservoir as the first fluid is pressurized, resulting in a mixture of the fluids in the second reservoir and in certain embodiments, increasing the time to reach the desired fluid flow rate. The reverse can occur when the second reservoir is pressurized greater than the first fluid reservoir. The mixture of fluids in a reservoir that results from this "backflow" of fluid from one reservoir to another may result in inaccuracies in the volumes of fluid delivered. According to embodiments, pressurization of the second fluid reservoir advancing the second drive member during pressurization of the first fluid reservoir by advancing the first drive member can minimize the backflow of the first fluid into the second fluid reservoir. In certain embodiments, the second drive member may be advanced at a rate equal to the rate of advancement of the first drive member so that the pressures in each reservoir are similar. Alternatively, the second drive member may be advanced at a rate less than the rate of advancement of the first drive member but at a sufficiently fast rate to minimize backflow mixing of the first fluid into the second reservoir. The rates of advancement of the second drive member relative to the rate of advancement of the first drive member may be determined by factors such as fluid types, differences in fluid viscosities, desired injection flow rates, conduit diameter including fluid line and catheter, use of dual flow protocols, dual flow ratios of fluids, system capacitance, system slack, length of fluid path, volume of fluid path, and the like. In closed systems, backflow concerns may be minimized due to the ability of the fluid injector to isolate other fluid reservoirs, for example by a controllable valve, can substantially minimize backflow of a pressurized fluid into a second fluid reservoir. According to various embodiments, with a closed fluid reservoir allows pressurization of the fluid within the fluid reservoir to substantially eliminate backflow of other pressurized fluid within the conduit when the fluid reservoir is placed in fluid communication with the conduit.

In other embodiments including a closed system, the target value may be greater than the first fluid pressure. According to these embodiments, pressurization of the second reservoir to a target value greater than the first fluid pressure may rapidly initiate the injection of the second fluid when the second reservoir is placed in fluid communication with the conduit, such that the fluid flow is kickstarted and/or prevents backflow into the second reservoir, which can lead to sharper boluses. Further, such higher target values may minimize effects of system compliance, for example, a portion of the pressure force of the first fluid swelling system components of the second reservoir.

In other embodiments, the target value may be less than the first fluid pressure. According to these embodiments, pressurization of the second reservoir to a target value less than the first fluid pressure may provide desired backflow prevention of the second fluid into the first reservoir and/or prevent over pressurization of the system. In other embodiments, the difference between the target value for the second fluid pressure relative to the first fluid pressure may be selected to provide an appropriate fluid flow ratio for a dual flow injection protocol or may more readily allow ramping to the desired dual flow ratio.

The target value may be determined by a processor associated with the fluid injector based on the specific fluid injection parameters and protocol, for example by calculation of the target value based on various factors, such as desired flow rates of the first fluid and second fluid, fluid types (e.g., contrast versus saline), system capacitance, whether dual flow injection is desired, whether backflow may be an issue, among other factors.

In certain embodiments where a dual flow injection protocol is desired, i.e., where the protocol requires a specific mixture of the first fluid and the second fluid to be injected concurrently, the step of advancing the second drive member to expel the second fluid from the second reservoir may further comprise continuing to advance the first drive member to expel the first fluid from the first reservoir to provide a dual flow fluid delivery of a predetermined ratio of the first fluid and the second fluid. The predetermined ratio may be a specified ratio ranging from 1:99 of the first fluid to the second fluid to 99:1 of the first fluid to the second fluid that may be pre-programmed into the processor by a user for a certain injection protocol or may be a predetermined or standard injection protocol that is provided by the manufacturer of the injector to provide the desired injection pattern.

In other embodiments, the method may further comprise isolating the first reservoir from fluid communication with the conduit prior to placing the second fluid reservoir in fluid communication with the conduit or, alternatively, prior to advancing the second drive member to expel the second fluid from the second reservoir in to the conduit. According to these embodiments, the injection protocol may include transitioning the injection from the first fluid to the second fluid while avoiding increases and/or fluctuations in fluid flow during the transition, for example when there is a difference in viscosity between the first fluid and the second fluid (such as a contrast media which can range from 2.0 to 30.0 cP (at 20° C.), to a lower viscosity fluid, such as saline having a viscosity of 1.0 to 1.5 cP (at 20° C.)), or avoiding backflow of the second fluid into the first fluid reservoir, or vice versa.

In other embodiments, the present disclosure provides a fluid delivery system configured for dynamic pressure control during a multiphase/multi-fluid injection, where the fluid delivery system comprises: at least a first reservoir configured for containing a first fluid; at least a second reservoir configured for containing a second fluid; a conduit connected to the first reservoir and the second reservoir for conducting fluid from the reservoirs to a patient; a fluid injector having at least a first drive member for expelling fluid from the first reservoir and at least a second drive member for expelling fluid from the second reservoir; and a controller in electronic communication with the fluid injector including computer readable memory. The controller may be associated with the fluid injector, a stand-alone operating computer, a removable operating storage media, a hospital information network, or outside computer. The memory includes instructions that when executed by the controller cause the controller to: instruct the injector to advance the first drive member to expel the first fluid from the first reservoir during a first injection phase, wherein the first fluid is pressurized to a first fluid pressure; measure the first fluid pressure during the first injection phase to provide a target value, wherein the target value is based on the measured fluid pressure of the first fluid phase; while the second reservoir is in fluid isolation from the conduit, instruct the injector to advance the second drive member to increase the fluid pressure of the second fluid in the second reservoir to the target value; instruct the injector to place the second reservoir in fluid communication with the conduit; and instruct the injector to advance the second drive member to expel the second fluid from the second reservoir into the conduit at a pressure equal to the target value.

Advantages of the various fluid pressure control methods according to various embodiments described herein include the ability to maintain flow rate across phase transitions. For example, this can maintain iodine flux across the phase transition which increases image enhancement relative to the same injection with a transient drop in flow rate. Therefore the pressure equalization is optimal use of a given contrast volume and flush, contrast volume and dual flow, contrast volume and subsequent contrast, etc. The pressure control methods may further provide a means to prevent backflow. By developing pressure in a subsequent phase reservoir, fluid from the first phase does enter the subsequent phase reservoir. By preventing backflow, bolus sharpness is improved relative to scenarios in which backflow mixing occurs. Further, pressure control methods, according to embodiments described herein, can be used to reduce over rate for scenarios in which a single reservoir is used across multiple phases during an injection to deliver fluid. For example if a reservoir delivers fluid at 200 psi during a phase and is subsequently closed by closing the valve, the 200 psi is trapped in the reservoir, for example as pressurized fluid and system capacitance. If the reservoir is used again during an injection, then the 200 psi of trapped pressure may be greater than the pressure of the intermediate phase leading to a fluctuation in fluid flow. Therefore, control of the pre-pressure can be used to reduce the trapped pressure, for example by appropriate advancement or retraction of the drive member, so that it is the same as the injection line pressure of the immediately preceding phase. Pressure control may also be used to remove system slack, for example mechanical slack and system compliance, generated by previous injection phases thereby maintaining volume accuracy across multiphase injections.

Referring to the drawings in which like reference characters refer to like parts throughout the several views thereof, the present disclosure is generally directed to fluid injector system and method for dynamic pressure control in a fluid injector. Associated disclosure related to capacitance development and issues associated with fluid injection system is described in PCT International Application No. PCT/US2017/020637, filed 3 Mar. 2017, the disclosure of which is incorporated herein by this reference.

With reference to FIG. 1, a fluid injector 10 (hereinafter referred to as "injector 10"), such as an automated or powered fluid injector, is adapted to interface with and actuate one or more syringes 12 (hereinafter referred to as "syringe 12"), which may be filed with a fluid F, such as contrast media, saline solution, or any desired medical fluid. The injector 10 may be used during a medical procedure to inject the medical fluid into the body of a patient by driving a plunger 14 of each syringe 12 with a drive member, such as piston 19 (shown in FIG. 2), such as linear actuator or a piston element. The injector 10 may be a multi-syringe injector having two, three or more syringes, wherein the several syringes 12 may be oriented in a side-by-side or other relationship and may be separately actuated by respective drive members/pistons 16 associated with the injector 10. In examples with two or more syringes, for example, arranged in a side-by-side or other relationship and filled with two different fluids, the injector 10 may be configured to deliver fluid from one or both of the syringes 12, sequentially or concurrently. According to one embodiment, the fluid injector 10 may be a dual head injector having two syringes 12a and 12b, a first syringe 12a for delivering a contrast media or other medical fluid and a second syringe 12b for delivering saline or other medically approved flushing agent to flush the contrast media to the patient. In other embodiments, the fluid injector 10 may have three syringes 12, a first and second syringe for delivering one or two different contrast media or other medical fluid and a third syringe for delivering saline or other medically approved flushing agent to flush the contrast media to the patient. According to various embodiments, the fluid injector 10 may be configured to deliver the contrast and saline separately (e.g., delivering a specific volume saline over a specific time followed by delivering a specific volume of contrast over a specific time, followed by a second volume of saline over a specified time to flush the contrast media from the tubing into the patient). According to various embodiments, the fluid injector 10 may be configured to deliver the contrast and saline separately or as a mixture (e.g., delivering a specific volume saline over a specific time followed by delivering a specific volume of contrast or a specified ratio of contrast and saline (i.e., in a "dual flow" process) over a specific time, followed by a second volume of saline over a specified time to flush the contrast media from the tubing into the patient). A technician may program a specific injection protocol into the injector (or use a pre-written protocol) to deliver the desired volumes of saline, contrast, specific ratios of contrast and saline mixtures, etc., at a desired flow rate, time, and volume for each solution. The fluid injector 10 may have at least one bulk fluid source (not shown) for filling the syringes 12 with fluid and in certain embodiments, the fluid injector 10 may have a plurality of bulk fluid source, one for each of the plurality of syringes, for filling each of the plurality of syringes with the desired fluid.

A conduit, such as a fluid path set 17, may be in fluid communication with each syringe 12 to place each syringe in fluid communication with a catheter for delivering the fluid F from each syringes 12 to a catheter (not shown) inserted into a patient at a vascular access site. In certain embodiments, fluid flow from the one or more syringes 12 may be regulated by a fluid control module (not shown) that operates various drive members, valves, stopcocks, and flow regulating structures to regulate the delivery of the saline solution and contrast to the patient based on user selected injection parameters, such as injection flow rate, duration, total injection volume, and ratio of fluids from the syringes 12, including specific ratios of each fluid in a dual flow injection protocol.

Figure 2:
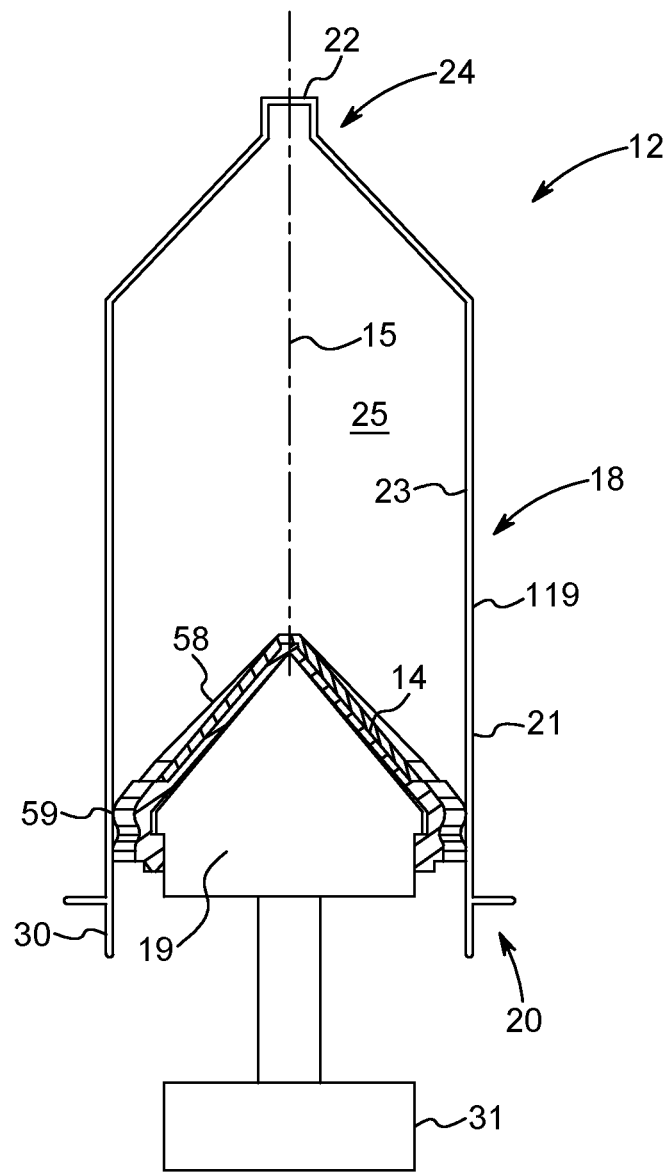
FIG. 2 is a side cross-sectional view of a syringe configured for use with the fluid delivery system of FIG. 1.

With reference to FIG. 2, the drive member 19, such as a reciprocally driven piston moved by a motor 31, may be configured to extend into and from the respective syringe port 13 through an opening in the front end of the injector housing. In fluid injector embodiments comprising a plurality of syringes, a separate drive member/piston 19 may be provided for each syringe 12. Each drive member/piston 19 is configured to impart a motive force to at least a portion of the syringe 12, such as the plunger 14 or a distal end of a rolling diaphragm syringe (for example, as described in PCT/US2017/056747; WO 2016/172467; and WO 2015/164783, the disclosures of which are incorporated herein by this reference). The drive member or piston 19 may be reciprocally operable via electro-mechanical drive components such as a ball screw shaft driven by the motor 31, a voice coil actuator, a rack-and-pinion gear drive, a linear motor, a linear actuator, and the like. The motor 31 may be an electric motor.

Examples of suitable front-loading fluid injectors 10 are disclosed in U.S. Pat. Nos. 5,383,858; 7,553,294; 7,666,169; 9,173,995; 9,199,033; and 9,474,857; and in PCT Application Publication No. WO 2016/191485 and WO 2016/112163, the disclosures of which are incorporated by reference in their entirety.

Having described the general structure and function of specific embodiments of the fluid injector 10, an embodiment of syringe 12 configured for use with the injector 10 will now be described with reference to FIG. 2. The syringe 12 generally has a cylindrical syringe barrel 18 formed from glass, metal, or a suitable medical-grade plastic, desirably a clear or substantially translucent plastic material. The material of the syringe 12 is desirably selected to meet the required tensile and planar stress requirements, water vapor transmission, and chemical/biological compatibility. The barrel 18 has a proximal end 20 and a distal end 24, with a sidewall 119 extending therebetween along a length of a longitudinal axis 15 extending through a center of the barrel 18. In some examples, the distal end 24 may have a conical shape that narrows in a distal direction from the cylindrical barrel 18. A nozzle 22 extends from the distal end 24. The barrel 18 has an outer surface 21 and an inner surface 23 with an interior volume 25 configured for receiving the fluid therein. The proximal end 20 of the barrel 18 may be sealed with the plunger 14 that is reciprocally movable through the barrel 18 by reciprocal movement of the corresponding piston 19 or drive member. The plunger 14 forms a liquid-tight seal against the inner surface 23 of the barrel 18 as the plunger 14 is advanced moved through the barrel 18.

In some examples, the proximal end 20 of the syringe 12 can be sized and adapted for being removably inserted in a syringe port 13 of the injector 10 (shown in FIG. 1). In some examples, the proximal end 20 of the syringe 12 defines an insertion section 30 that is configured to be removably inserted into the syringe port 13 of the injector 10 while the remaining portion of the syringe 12 remains outside of the syringe port 13.

Figure 3:
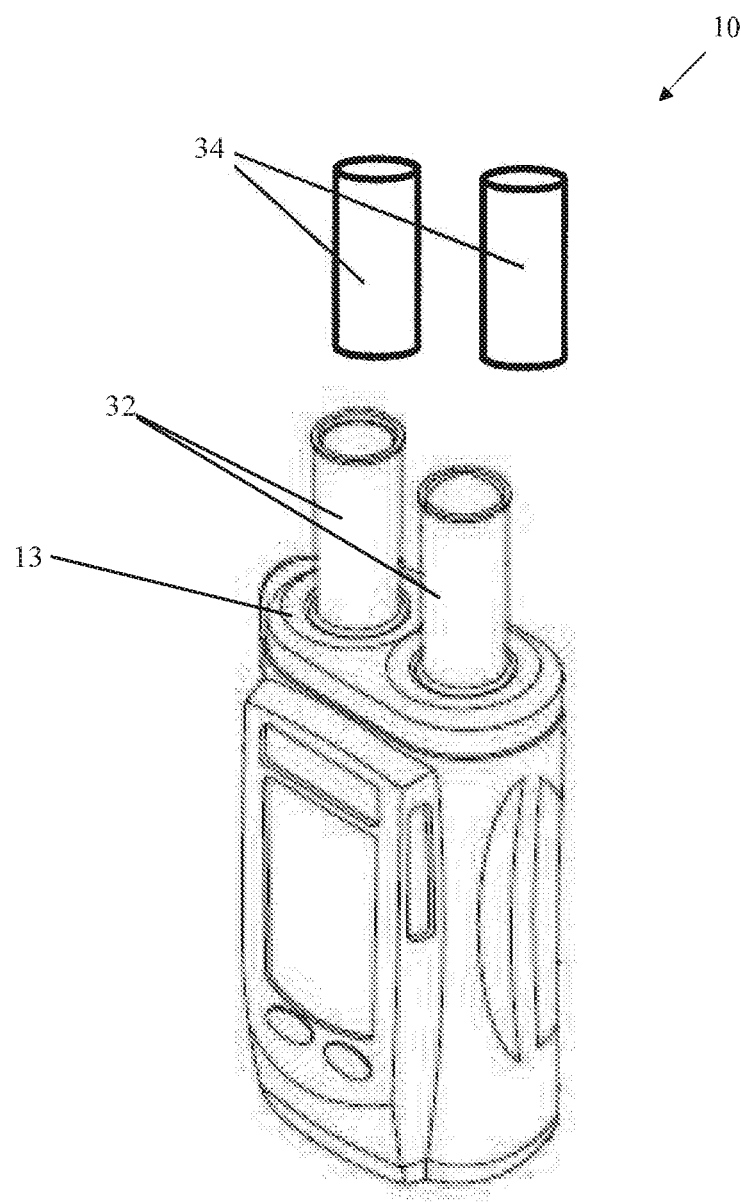
FIG. 3 is a perspective view of a fluid delivery system according to another example of the present disclosure.

In some examples, such as shown in FIG. 3, the injector 10 may be configured for receiving and retaining a pressure jacket 32 within each syringe port 13 of the injector 10. While FIGS. 1 and 3 illustrate fluid injectors 10 with two syringe ports 13, which for the injector 10 shown in FIG. 3 each having a corresponding pressure jacket 32, other examples of the fluid injector 10 may include a single syringe port 13 and optionally, a corresponding pressure jacket 32 or more than two syringe ports 13 with an optional corresponding number of pressure jackets 32. In embodiments comprising pressure jackets, each pressure jacket 32 may be configured to receive a syringe, such as a syringe for an angiographic (CV) procedure, or a rolling diaphragm syringe 34 (suitable examples of which are described in described in PCT/US2017/056747; WO 2016/172467; and WO 2015/164783). A fluid path set, similar to the fluid path set 17 shown in FIG. 1, may be fluidly connected with a discharge end of each rolling diaphragm syringe 34 for delivering fluid from the syringes 34 through tubing connected to a catheter, needle, or other fluid delivery connection (not shown) inserted into a patient at a vascular access site. According to various embodiments, the syringe 12 or 34 may be a pre-filled syringe, i.e., the syringe may be prefilled with a medical fluid, such as a contrast agent or saline, when provided by the syringe manufacturer. According to certain embodiments, the pre-filled syringe may be required to be spiked or otherwise punctured at the discharge end prior to an injection procedure to allow fluid to be expelled from the syringe into a fluid line to the patient, as described herein.

Figure 4:
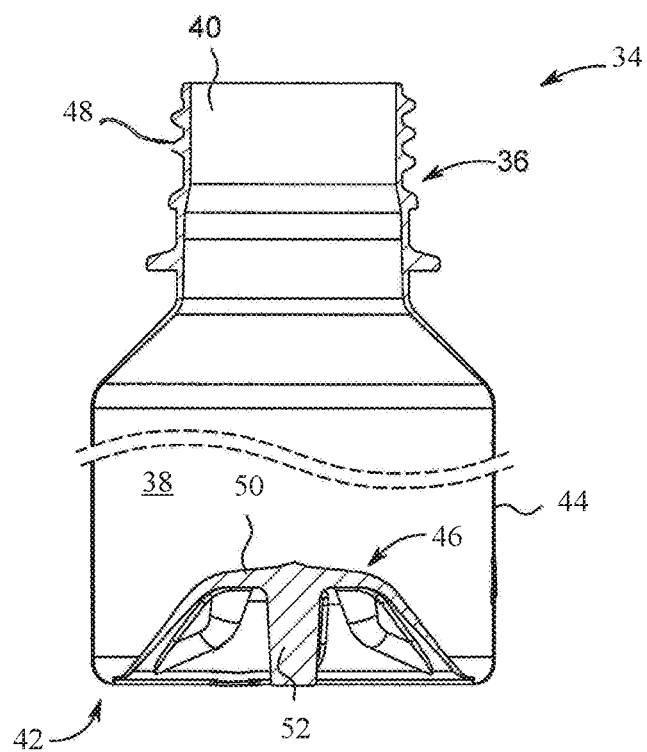
FIG. 4 is a side cross-sectional view of a syringe configured for use with the fluid delivery system of FIG. 3.

With reference to FIG. 4, the rolling diaphragm syringe 34 generally includes a hollow body 36 defining an interior volume 38. The body 36 has a forward or distal end 40, a rearward or proximal end 42, and a flexible sidewall 44 extending therebetween. The proximal end 42 may be configured to act as piston to pressurize the syringe interior to draw in or expel fluid therefrom, as described herein. The sidewall 44 of the rolling diaphragm syringe 34 defines a soft, pliable or flexible, yet self-supporting body that is configured to roll upon itself, as a "rolling diaphragm", under the action of the a drive member or piston of the fluid injector 10. The drive member/piston 19 may be configured to releasably engage a drive member engagement portion 52 at the proximal end 42 of the rolling diaphragm syringe 34 (examples of which are described in PCT/US2017/056747). In operation, the sidewall 44 is configured to roll such that its outer surface is folded and inverted in a radially inward direction as the drive member/piston 19 moves the proximal end 42 in a distal direction and unrolled and unfolded in the opposite manner in a radially outward direction as the drive member/piston 19 retract the proximal end 42 in a proximal direction.

With continued reference to FIG. 4, the rearward or proximal portion of the sidewall 44 connects to a closed end wall 46, and a forward or distal portion of the sidewall 44 defines a discharge neck 48 opposite the closed end wall 46. The closed end wall 46 may have a concave shape to facilitate the initiation of the inversion or rolling of the sidewall 44, enhance mechanical strength of the closed end wall 46, and/or to provide a receiving pocket to receive a distal end of drive member/piston 19. For example, the closed end wall 46 may define a receiving end pocket for interfacing directly with a similarly-shaped distal end of the drive member/piston 19. In some examples, at least a portion of the drive member/piston 19 may be shaped to substantially match the shape of the closed end wall 46 or, alternatively, pressure from the drive member/piston 19 as it is moved distally may conform the end wall 46 to substantially match the shape of at least a portion of the drive member/piston 19.

The end wall 46 may have a central portion 50 having a substantially dome-shaped structure and a drive member engagement portion 52 extending proximally from the central portion 50. The drive member engagement portion 52 is configured for releasably interacting with a corresponding engagement mechanism on the drive member/piston 19 of the fluid injector 10, for example as the drive member/piston is retracted. The rolling diaphragm syringe 34 may be made of any suitable medical-grade plastic or polymeric material, desirably a clear or substantially translucent plastic material. The material of the rolling diaphragm syringe 34 is desirably selected to meet the required tensile and planar stress requirements, water vapor transmission, and chemical/biological compatibility.

Figure 5:
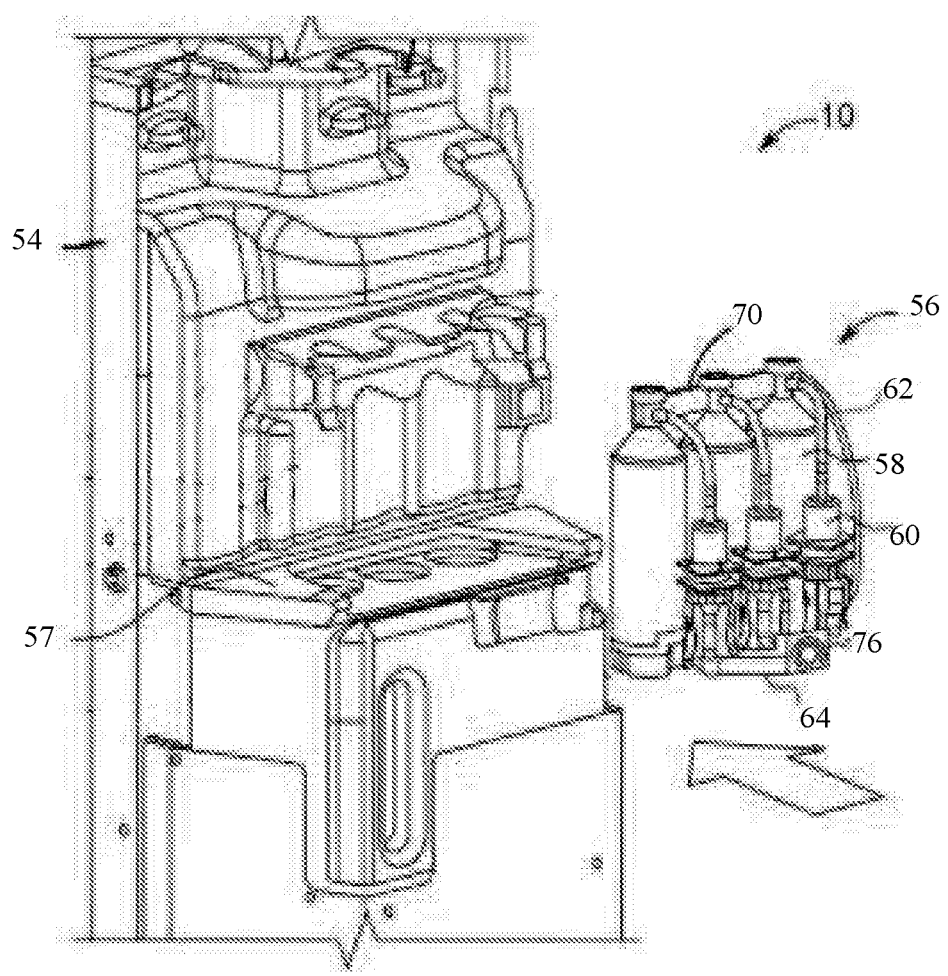
FIG. 5 is a perspective view of a fluid delivery system according to another example of the present disclosure.
Figure 6:
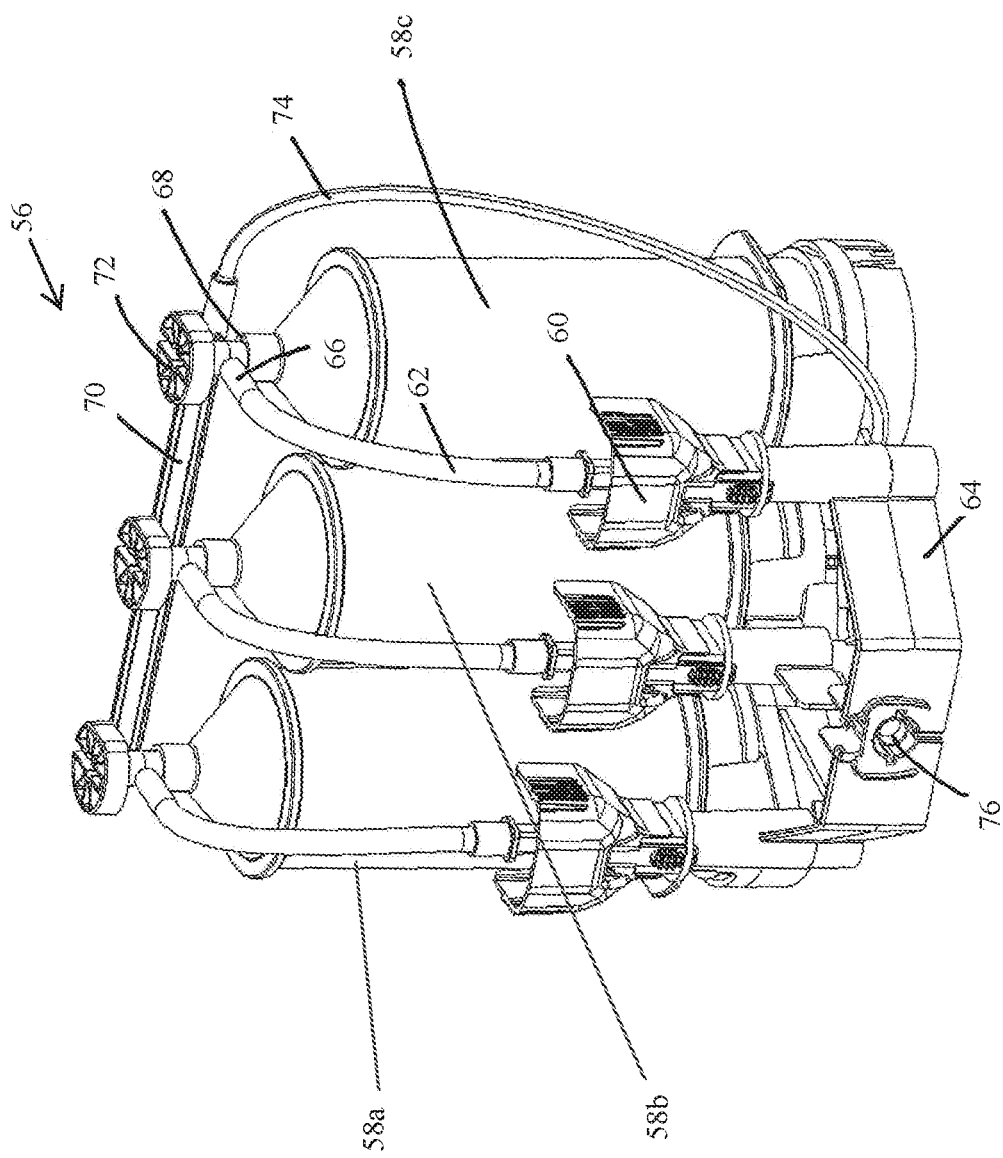
FIG. 6 is a front perspective view of a multi-use disposable system configured for use with the fluid delivery system of FIG. 5.

With reference to FIG. 5, a fluid injector 10 is shown in accordance with another example of the present disclosure. The injector 10 has a housing 54 that encloses various mechanical drive components, electrical and power components necessary to drive the mechanical drive components, and control components, such as electronic memory and electronic control devices used to control operation of reciprocally movable pistons (not shown). The fluid injector 10 further has a multi-patient disposable system (MUDS) 56 that is removably connectable with the fluid injector 10. The MUDS 56 has one or more syringes or pumps 58. In some aspects, the number of syringes 58 corresponds to the number of pistons on the fluid injector 10. In some examples, such as shown in FIG. 6, the MUDS 56 has three syringes 58a-58c in a side-by-side arrangement. Each syringe 58a-58c has a bulk fluid connector 60 for connecting to a respective bulk fluid source (not shown) via a MUDS fluid path 62. The MUDS fluid path 62 may be formed as a flexible tube with a spike element at its terminal end that connects to the bulk fluid connector 60. Injector 10 and the corresponding MUDS 56 as illustrated in FIG. 5 are described in detail in WO 2016/112163, the disclosure of which is incorporated herein by this reference.

The MUDS 56 may comprise one or more syringes or pumps 58a-58c. In some aspects, the number of syringes 58 corresponds to the number of drive members/pistons on the fluid injector 10. In some examples, such as shown in FIGS. 5 and 6, the MUDS 56 has three syringes 58a-58c arranged in a side-by-side arrangement. Each syringe 58a-58c has a bulk fluid connector 60 for connecting to a respective bulk fluid source (not shown) via a MUDS fluid path 62. The MUDS fluid path 62 may be formed as a flexible tube that connects to the bulk fluid connector 60 having a spike element at its terminal end.

With reference to FIG. 6, the MUDS 56 has a frame 64 for supporting the one or more syringes 58a-58c. The syringes 58a-58c may be removably or non-removably connected to the frame 64. Each syringe 58a-58c has an elongated, substantially cylindrical syringe body. Each syringe 58a-58c has a filling port 66 in fluid communication with the MUDS fluid path 62 for filling the syringe 58a-58c with fluid from a bulk fluid source. Each syringe 58a-58c further has a discharge outlet or conduit 68 at the terminal portion of its distal end. The discharge outlet 68 of each syringe 58a-58c is in fluid communication with a manifold 70. A valve 72 is associated with each discharge outlet 68 and is operable between a filling position, where the filling port 66 is in fluid communication with the syringe interior while the discharge outlet 68 is in fluid isolation from the syringe interior, and a delivery position, where the discharge outlet 68 is in fluid communication with the syringe interior while the filling port 66 is in fluid isolation from the syringe interior. The manifold 70 has a fluid pathway that is in fluid communication with each syringe 58a-58c and with a fluid outlet line 74 in fluid communication with a port 76 configured for connecting to a single use fluid path element (not shown) for delivering fluid to the patient.

In various embodiments, for fluid injector 10, for example any of the fluid injectors shown in FIGS. 1, 3, and 5, the motor 31 (FIG. 2) provides the motive force to reciprocally drive the drive member/piston 19 in a distal direction and discharges fluid within the syringes 12, 34 or MUDS 56. The motor 31 may have drive components, such as gears and shafts, that are operatively connected to the drive member/piston 19 to reciprocally move the drive member/piston 19. Each motor 31 must be calibrated to correlate its operating characteristics, such as input current or output torque, to a flow rate or pressure and tolerances associated therewith. As described herein, calibration may be desirable to compensate for any variations or out of specification behavior from any of the different components of the fluid injectors 10, such as any variations in motor performance characteristics, particularly in fluid injectors with two or more syringes driven by two or more motors. For example, conversion of motor input torque for one motor 31 to an injector output pressure may be different for another motor 31. This variation may be further compounded by variations in tolerances of the drivetrain of the fluid injector 10. The accuracy of flow rate or pressure in a fluid injector 10 is directly correlative to a system and method used to calibrate the motor 31.

According to one example of the present disclosure, the fluid injector 10 discussed above with respect to FIGS. 1-6 may be configured to perform a multi-phase fluid injection which includes an injection of a first fluid F1 during a first phase, followed by an injection of a second fluid F2 during a second phase. During the first phase, the first fluid F1 is injected from at least a first syringe, for example the syringe 12a of FIG. 1 or one of the syringes 58b and/or 58c of FIGS. 5-6. During the second phase, the second fluid F2 is injected from at least a second syringe, for example the syringe 12b of FIG. 1 or syringe 58a of FIGS. 5-6. Hereinafter, the first and second syringes will be discussed with reference to FIGS. 5-6, and will thus be referred to as the first syringe 58b and the second syringe 58a. However, it is to be understood that the systems and methods described herein are equally applicable to any of the syringes 12a-12b of FIG. 1, an injector with two or more rolling diaphragm syringes 34 as illustrated in in FIGS. 3-4, or any other set of least two syringes in a fluid injection system.

The first fluid F1 of the first syringe 58b and the second fluid F2 of the second syringe 58a may be different fluids, such as medical fluids having different properties, such as different viscosities. Alternatively the first fluid F1 and the second fluid F2 may be the same fluid, for example medical fluid but at different concentrations or temperatures, or the same fluid being delivered at a different flow rate. For example, the first and second fluids F1, F2 may have one or more of a different viscosity, temperature, and/or density. In one example of the present disclosure, the first fluid F1 may be contrast media, as described herein, having a first viscosity and the second fluid F2 may be saline having a second viscosity which is typically lower than the first viscosity. In certain embodiments, the fluid injector may have a third syringe 58c, which may contain a third fluid F3 that may be the same or different that the first fluid F1 and second fluid F2. For example, F3 may be a contrast media, which may be the same as first fluid F1 or F3 may be a different contrast agent than F1, or F3 may be the same contrast type as F1 but at a different concentration than F1. During the first phase of the multi-phase injection, the first fluid F1, i.e. contrast, may be injected from the first syringe 58b at a first predetermined flow rate programmed into the injector 10. Delivery of the first fluid F1 at the first predetermined flow rate is achieved by applying a pressure to the first fluid F1 in the first syringe 58b, such as by driving the plunger of the first syringe 58b with the piston 19, where the necessary applied pressure to achieve the desired first predetermined flow rate is a function of the first viscosity of the first fluid F1. Because of the generally higher viscosity of the contrast of the first fluid F1, higher applied pressures are generally required to achieve a predetermined flow rate compared to the necessary applied pressure to achieve the same flow rate for a fluid with a lower viscosity, such as saline. Following the first phase of the multi-phase injection, the second phase includes injection of the second fluid F2, i.e. saline, from the second syringe 58a. The second predetermined flow rate of the second fluid F2 may be the same as, greater than, or lower than the first predetermined flow rate of the first fluid F1. In fluid injections where the first and second predetermined flow rates are targeted to be the same, due to the differences between the first viscosity of the first fluid F1 and the second viscosity of the second fluid F2, the pressure required to deliver the second fluid F2 may differ from the pressure required to deliver the first fluid F1. In the present example, the pressure applied to the first fluid F1, i.e. contrast media, is generally higher than the pressure applied to the second fluid F2, i.e. saline, in order to obtain the same flow rate. In other examples, the second predetermined flow rate of the second fluid F2 may be different than the first predetermined flow rate of the first fluid F1, yet the pressures necessary to achieve the predetermined flow rates of the first fluid F1 and the second fluid F2 may still be different.

Figure 7:
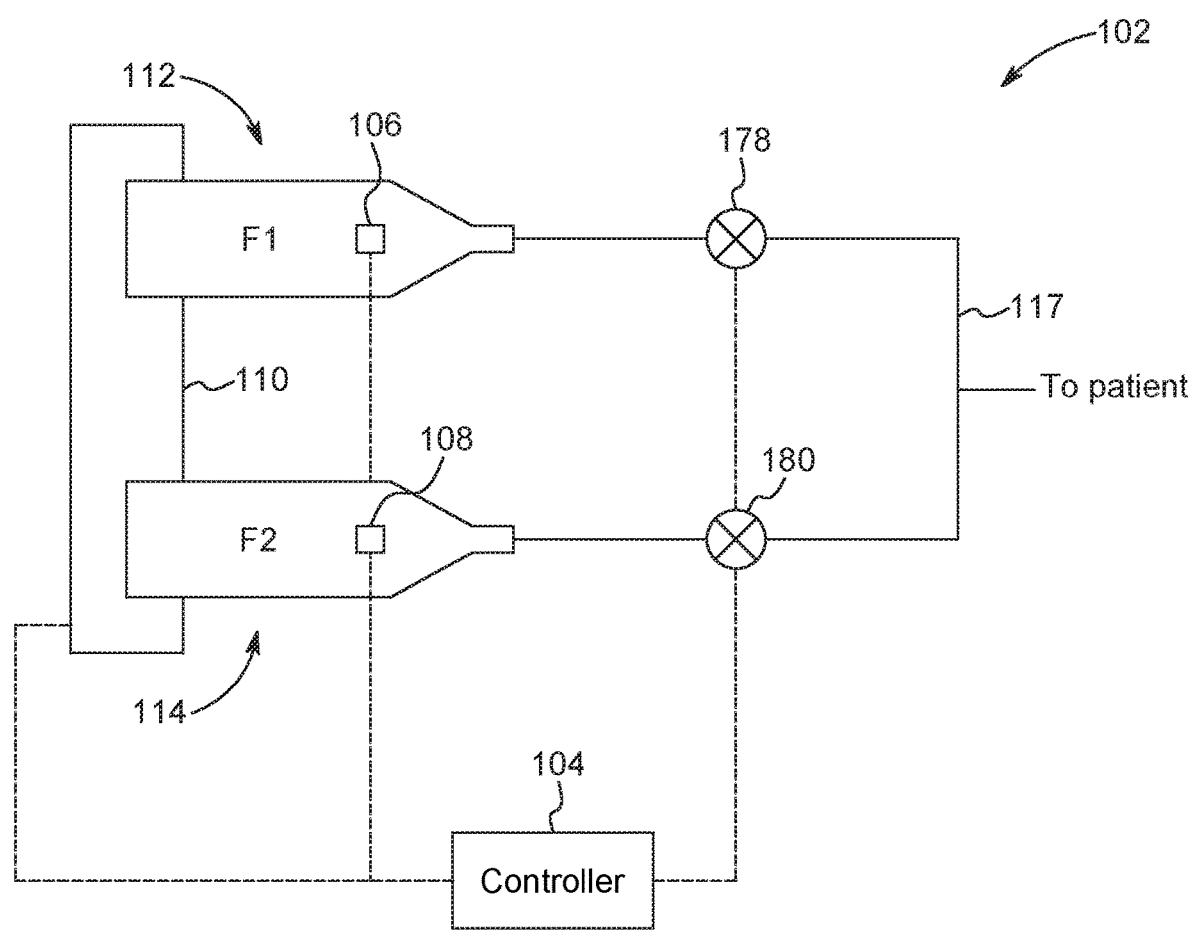
FIG. 7 is a schematic drawing of another example of a fluid delivery system.

A schematic drawing of a fluid delivery system 102 similar to the systems 10 shown in FIGS. 1, 3, and 6, is shown in FIG. 7. The system 102 includes a first reservoir, such as a first syringe 112, containing a first fluid F1. In some examples, the first fluid F1 may be a contrast agent, as is commonly used in a first or contrast phase of a multiphase injection. The system 102 also includes a second reservoir, such as a second syringe 114, containing a second fluid F2. For example, the second fluid F2 can be a saline fluid used in a second or saline flush phase of a multiphase injection. Alternatively the second fluid may be the same as the first solution, i.e., both solutions may be a contrast agent having the same or different concentrations. The system 102 also includes a conduit 117, such as medical tubing, a fluid path set, manifold, or similar fluid conducting structures, for conveying fluid from the first syringe 112 and the second syringe 114 to a patient. For example, the conduit 117 is connected to a patient catheter for fluid delivery to a patient's vein at a vascular access site. The conduit 117 can be similar in structure and function to the fluid path set 17 (shown in FIG. 1) or to the manifold and fluid path shown in the MUDS fluid path set 62 (shown in FIG. 6).

In some examples, the system 102 also includes a fluid injector 110 configured to receive the syringes 112, 114, or MUDS 56. The syringes 112, 114 can be front loading syringes having a movable plunger for expelling fluid therefrom, rolling diaphragm syringes as previously described, or other types of disposable or reusable syringes as are known in the art. The injector 110 can be similar to the front loading injector 10 (shown in FIG. 1) or to the multi-patient injector 10 (shown in FIG. 6). The fluid injector 110 can include independent drive members 119, such as a moveable piston or linear actuator, for expelling fluid F1, F2 from the syringes 112, 114. For example, as previously described, drive members can be configured to engage a plunger of the syringes 112, 114 and to advance the plunger through a barrel of the syringe 112, 114 in an axial direction to expel fluid therefrom.

In some examples, the system 102 further includes a fluid control device, such as valves 178, 180 for restricting fluid flow between the syringes 112, 114 and conduit 117. Valves for regulating fluid flow through the system 102 can include, for example, stopcocks, check valves, ball valves, diaphragm valves, and other types of manually or automatically actuatable valves, as are known in the art. In some examples, valves for different syringes can be combined into a single manifold device, such as the manifold 70, shown in FIG. 6. In other examples, valves 178, 180 can be separate structures or devices that can be operated independently by a user. The valves 178, 180 are configured to transition between a closed position, in which fluid flow between the syringe 112, 114 and the conduit 117 is prevented, to an open position, in which fluid flow is permitted. In other embodiments, the valves 178, 180 may be configured to further control fluid flow by being partially open to control the orifice size through which the fluid flows from the reservoir. In other embodiments of the fluid injections, there may be no valves in the system. In some examples, valves 178, 180 are connected to a nozzle of each syringe 112, 114 and/or between the syringe nozzle and the conduit 117 to prevent fluid from passing between the syringe 112, 114 and the conduit 117 when the valve 178, 180 is in the closed position. In other examples, valves 178, 180 can be positioned in the conduit 117 and open and close to restrict fluid flow therethrough.

Figure 12A:
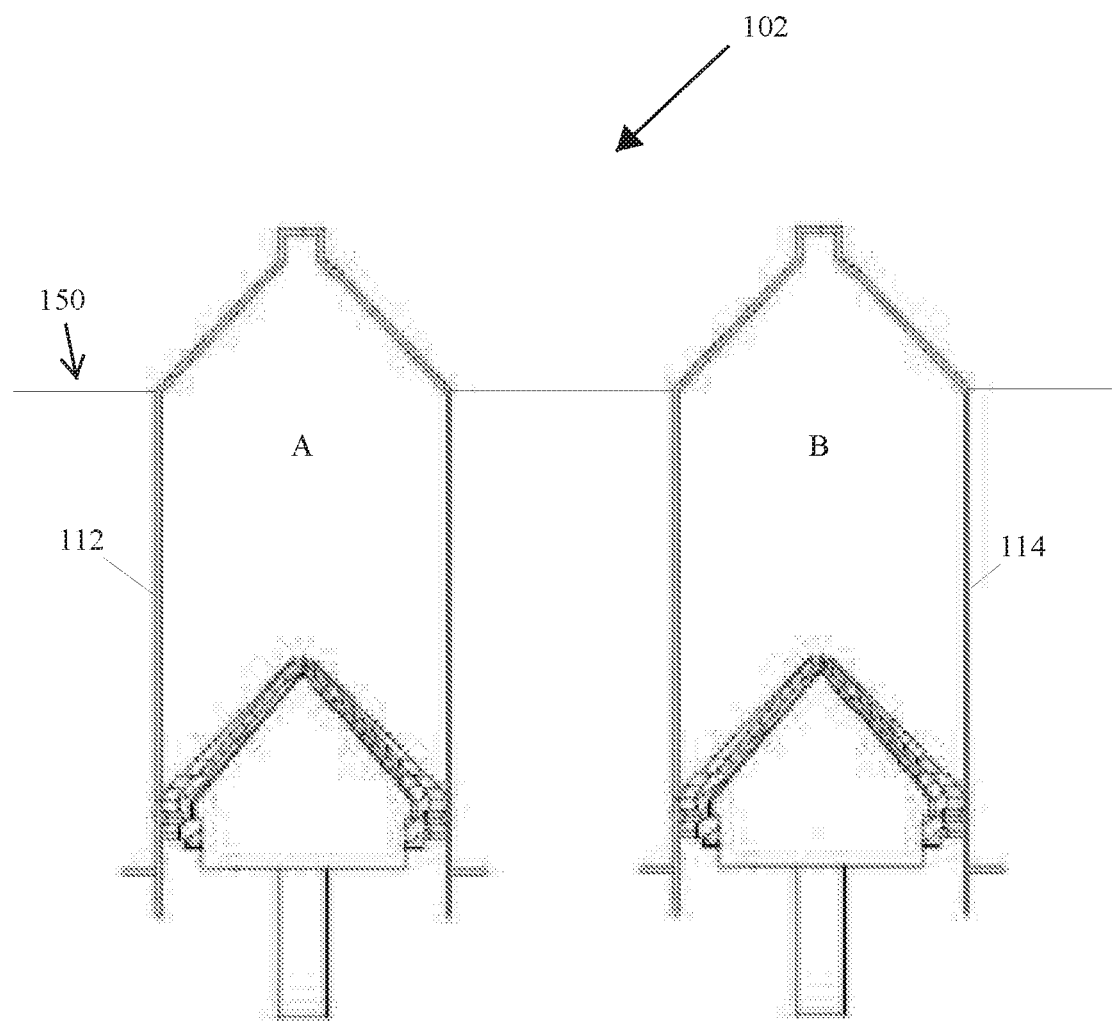
FIGS. 12A and 12B are schematic drawings illustrating slack caused by displacement of syringes during an injection.
Figure 12B:
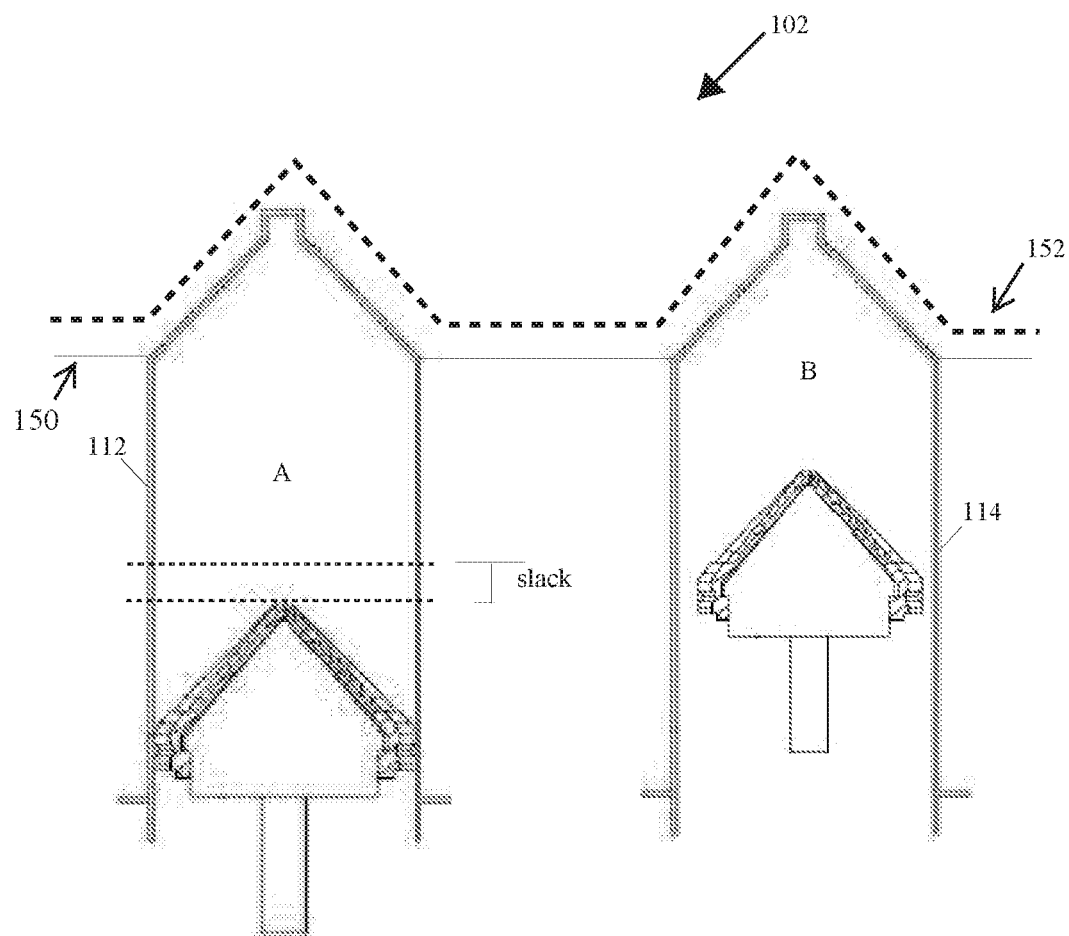

In some examples, the system 102 further comprises sensors 106, 108 associated with the first syringe 112 and/or the second syringe 114 or with the fluid path associated with each syringe. Various different types of sensors can be used for measuring information about syringe type, fluids F1, F2 contained in the syringes 112, 114, injection parameters for an injection being performed, or environmental conditions (e.g., ambient temperature) near the injector 110. In some examples, the sensors 106, 108 can be fluid pressure transducers, pressure gauges, strain gauges, or sensors configured to measure fluid pressure in the syringes 112, 114 or conduit 117. Syringe pressure can also be measured by monitoring motor current of the injector 110 to determine force required for driving the plunger through the syringe barrel. According to various embodiments, pressure control can be used to eliminate slack that develops during an injection. As an example, the syringe(s) may display compliance or impedance under pressurization, such as where the syringe stretches axially, injector/syringe interfaces deflect and/or displace, or the restraints bend. This causes slack as the piston can move away from the plunger on a non-injecting reservoir/syringe. A schematic representation of a fluid delivery system 102 illustrating slack due to deflection of syringe components during an injection is shown in FIGS. 12A and 12B. As shown in FIG. 12A, prior to the injection, the syringes 112, 114 are attached to and restrained by a restraint structure 150. As shown in FIG. 12B, pressure from the piston and plunger during the injection causes the syringes 112, 114 to stretch or displace by a small amount as a result of increased pressurization. For example, the syringes 112, 114 may be stretched or displaced by an axial distance indicated by the dashed line 152, which represents an amount of slack or slack distance for the syringes 112, 114 as a result of the injection.

In some examples, the system 102 further includes a controller 104 in electrical communication with the injector 110, valves 178, 180, sensors 106, 108, and other components of the system 102. The controller 104 is generally configured to control an injection process by actuating the drive member(s) of the injector 110 to control fluid delivery. The controller 104 can also be configured to record information about an injection procedure and, in some instances, to control transmission of recorded information to remote sources through a transceiver or communications device associated with the controller 104, as are known in the art. The controller 104 can be a computer processor or processing device associated with computer readable memory for operating components of the fluid delivery system 102. In some examples, the controller 104 is an electronic component of the injector 110 contained within the injector housing. In that case, the controller 104 can be configured to control or manage other electrical components of the injector 110, such as a visual display, control panel, user input device, and others. In other examples, the controller 104 can be a separate electronic device, such as a computer tablet, smart phone, or personal computer, in electrical communication with the injector 110. In that case, the controller 104 can be configured to receive information and instructions from the injector 110, sensors 106, 108, or valves 178, 180, process the received information, and transmit instructions to components of the system 102 based on the processing information. In some examples, as described in connection with FIG. 8, the controller 104 can be configured to manage a dynamic pressure control process in the fluid delivery system to ensure that fluid is provided as a substantially continuous fluid stream without pressure drops or other discontinuities.

Figure 8:
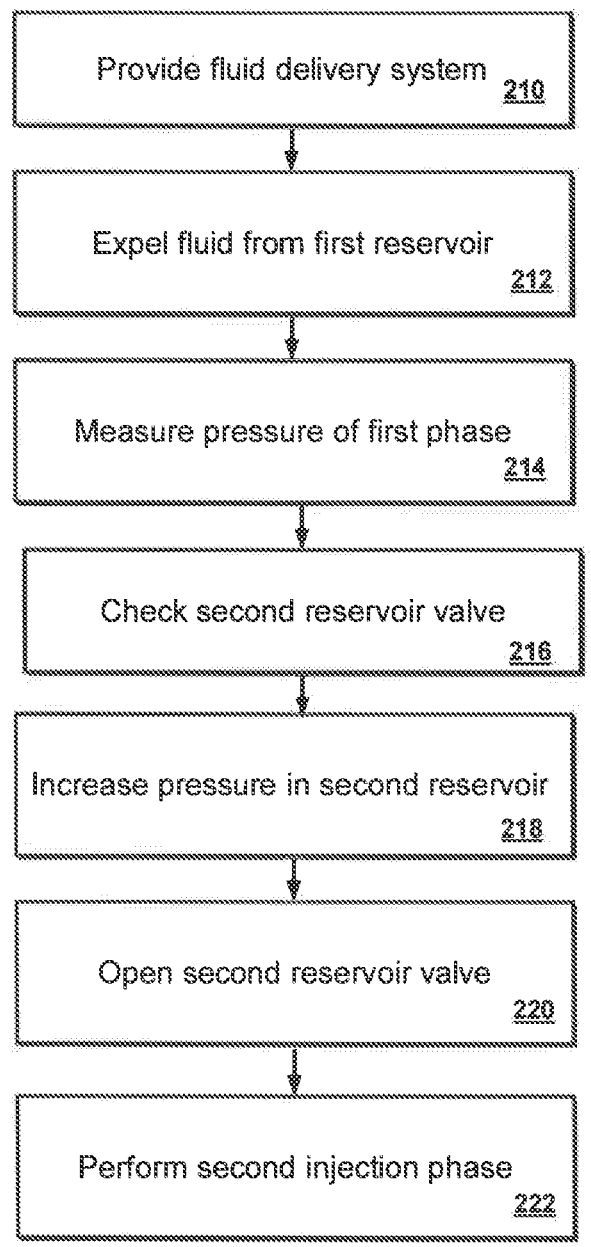
FIG. 8 is a flow chart of a fluid delivery method with dynamic pressure control according to an example of the present disclosure.

With reference to FIG. 8, a method or process for dynamic pressure control for a fluid delivery system is depicted. The method or process is adapted to pre-pressurize or preload fluid reservoirs and/or to preload the drive members or pistons of a fluid injector to account for compliance and/or system slack developed in a fluid delivery system during a preceding injection phase in order to maintain constant flow rate across a phase transition. For example, the method or process disclosed herein can be adapted to reduce or eliminate slack between a first or contrast phase of an injection and a second or saline flush phase of the injection. The method or process can also eliminate pressure differential between an injecting line (e.g., fluid conduit or fluid path set)

and isolated fluid reservoirs using compliance characterizations and/or real time pressure monitoring in order to prevent cross contamination of fluid reservoirs.

In some examples, the method includes providing a multiphase fluid delivery system as shown at step 210. The multiphase fluid delivery system can include components of the systems, injectors, and syringes shown in FIGS. 1-7. For example, a fluid delivery system can include a first fluid reservoir, such as a disposable or multi-use syringe or syringe set including an elastomeric plunger for expelling fluid therefrom. In specific embodiments, the first fluid reservoir can also include a rolling diaphragm syringe as described herein. The reservoir can contain a first fluid. The fluid delivery system can also include a second fluid reservoir, such as a syringe, containing a second fluid, which may be the same fluid or a different fluid from the fluid contained in the first reservoir, and a fluid conduit, such as a fluid path set, for conducting fluid from the first reservoir and the second reservoir. The system also includes an injector including a first drive member for expelling fluid from the first reservoir and a second drive member for expelling fluid from the second reservoir.

As shown at step 212, the process includes advancing the first drive member to expel fluid from the first reservoir into the conduit during a first injection phase. For example, a user may actuate the first drive mechanism by pressing an appropriate button or control dial on the injector to cause a piston or linear actuator to advance towards a plunger of the syringe, engage the plunger, and advance the plunger through the syringe to expel fluid therefrom. As shown at step 214, a fluid pressure of the injection is measured during the first injection phase. Fluid pressure can be measured by a pressure transducer or strain gauge positioned in a barrel of the syringe or in a portion of the conduit or fluid path set. In other examples, fluid pressure can be measured indirectly, such as by measuring fluid flow rate through the syringe and/or conduit and determining pressure based on fluid density. In other examples, pressure can be determined based on motor current drawn by the injector. In some examples, fluid pressure is measured continually during an entire first injection phase, as occurs, for example, when using an analog gas gauge. In other examples, fluid pressure can be measured periodically, such as at predetermined intervals during the first injection phase.

During the first injection phase, in one embodiment, as shown at step 216, the system may be configured to ensure that the valve connected to or associated with the second syringe is in a closed position and/or that the second syringe is not in fluid communication with the conduit, so that the second reservoir can be pressurized by movement of the piston and plunger. In other examples, the valve does not need to be closed. In that case, the piston can move forward to generate a matching pressure (e.g., a pressure which matches the first phase pressure). However, leaving the valve open may result in fluid mixing depending on fluid properties and orientation of fluid, among other factors. In other examples, in order to reduce or eliminate mixing, a valve, such as a stopcock, can be partially opened to some small opening size and the piston can be moved forward to generate the desired pressure. In other examples, pinch valves, roller valves, or clamps can be used in place of a stopcock.

In another embodiment, while the second reservoir or syringe is not in fluid communication with the conduit, as shown at step 218, the second drive member is advanced through the second reservoir to increase fluid pressure in the second reservoir. The drive member continues to advance until fluid pressure in the second reservoir increases to a target value determined based on the measured fluid pressure during the first injection phase. In some examples, the target value is equal to the previously measured fluid pressure during the first injection phase. In other examples, the target value can be a percentage of the previously measured pressure value. For example, the target value can be between about 0% and 200% of the previously measured fluid pressure. For instance, if the measured injection pressure is 100 psi and the target is about 80%, then the second reservoir piston will move until the pressure is 80 psi.

In some examples, fluid pressure in the second reservoir or syringe may be measured using an electronic pressure transducer or sensor in fluid communication with the reservoir. In that case, a system controller can be configured to continue to advance the drive member of the injector until a measurement by the sensor confirms that the target pressure has been obtained. When the target pressure is obtained, the controller can be configured to provide an instruction to the injector to cause the injector to stop advancing the drive member. In other examples, a final position of the drive member and/or syringe plunger can be calculated based on the measured fluid pressure during the first injection phase and a present position of the drive member. For example, the controller can be configured to obtain information about a position of the drive member and desired final fluid pressure. The controller can calculate how far the plunger must be advanced to obtain the target pressure. In other examples, if the first fluid injecting pressure decreases, the drive piston can move backwards/retract, for example at a constant rate or a stepped rate, to reduce the pressure in accordance with the target pressure. The controller can then cause the drive mechanism to advance the plunger the calculated distance. In this way, the controller can cause the syringe pressure of the second syringe to increase without needing to continuously or periodically measure fluid pressure of the second syringe. In various embodiments, measurement of the pressure of the second fluid in the second reservoir may not be needed during this process.

Once the target fluid pressure in the second syringe is obtained, the fluid delivery system is ready to begin delivery of the second fluid or contrast to the patient (e.g., the second injection phase). Factors other than pressure may also be relevant for determining when to begin the second injection phase. However, in most examples, the second injection phase should only start once the target pressure is reached. In order to perform the second injection phase, as shown at 220, the valve is manually or automatically opened to establish fluid communication between an interior of the second reservoir and the fluid conduit or fluid path set. Once the valve is opened, the drive member can continue to advance to expel fluid from the second reservoir and to the conduit as shown at step 222. Optionally, the valve for the first syringe may be closed to isolate the first syringe from the fluid path or, alternatively, partially closed to allow pressure control between the syringes while minimizing mixing of the second fluid with the first fluid in the first syringe.

For example according to a non-limiting example of a 3-phase injection protocol, such as a contrast—saline—contrast injection protocol, the first contrast phase may generate a pressure of 100 psi, which the second saline phase may generate a pressure of 20 psi. When transitioning from contrast to saline, the 100 psi of the contrast pressure is trapped in the contrast reservoir after the contrast reservoir is fluidly isolated with a valve, and the saline phase starts at 100 psi, due to matching the pressure in the fluid line, and then falls to 20 psi. During the saline phase injection, the trapped pressure in the contrast reservoir must be lowered to the pressure of the saline, i.e., 20 psi, so that at the start of the third phase (second contrast phase) the pressure of the contrast in the third phase matches the 20 psi system pressure from the saline phase, thereby eliminating flow rate fluctuations and potential backflow of contrast into the saline reservoir. At the end of the injection protocol, all reservoirs may be fluidly isolated by the corresponding valves and the pressure within each reservoir returned to 0 psi to prepare the system for the next injection protocol.

A pressure control process, as described herein, provides several benefits for a multiphase injector system compared to processes without pressure control. For example, driving the second drive member or piston forward to increase pressure of the second fluid reservoir or syringe ensures that the plunger of the second syringe remains in contact with the fluid for any subsequent phase. Further, driving the plunger of the second syringe forward eliminates slack introduced into the system due to movement of the disposable syringes during a previous injection phase, thereby improving volume accuracy and eliminating decreases in flow rate at the phase transition.

Pressurizing a subsequent injection phase, such as the saline or second phase of an injection process, also removes a compliance of the isolated second reservoir. Removing compliance of the second reservoir ensures that all piston movement during the subsequent phase results in fluid delivery rather than expansion of the system. This also minimizes or eliminates any dip in flow rate when transitioning from one injection phase to another, as shown by the graphs in FIGS. 9-11.

In some examples, the pressure control process described herein can also be adapted for use with a single syringe. In other examples, injection systems having more than two syringes and for injection processes including a dual flow phase. Beneficially, the pressure control process improves dual flow ratio accuracy since fluid is delivered from pressurized reservoirs during the entire dual flow phase. In contrast, when pressure control is not performed, a portion of the phase is spent taking up system compliance.

In some examples, pressure control can be performed for the first phase of an injection or with a single syringe injection. The target pressure can be a set value (for example 100 psi) or can be determined based on the compliance of the system. Beneficially, pre-pressurizing the first injection phase would remove the ramp time required to reach the desired flow rate. Pre-pressurizing the first injection phase would also result in a sharper bolus. See FIG. 9, second injection phase 318.

According to other aspects, the pressure control process prevents cross contamination between fluid reservoirs, which provides a sharper bolus/transition as the concentration of contrast or saline remains pure in the respective reservoir. Avoiding cross-contamination between fluid reservoirs is important for multi-patient systems in which cross-contamination of fluid reservoirs would accumulate throughout the use life of the system.

EXAMPLES

Figure 9:
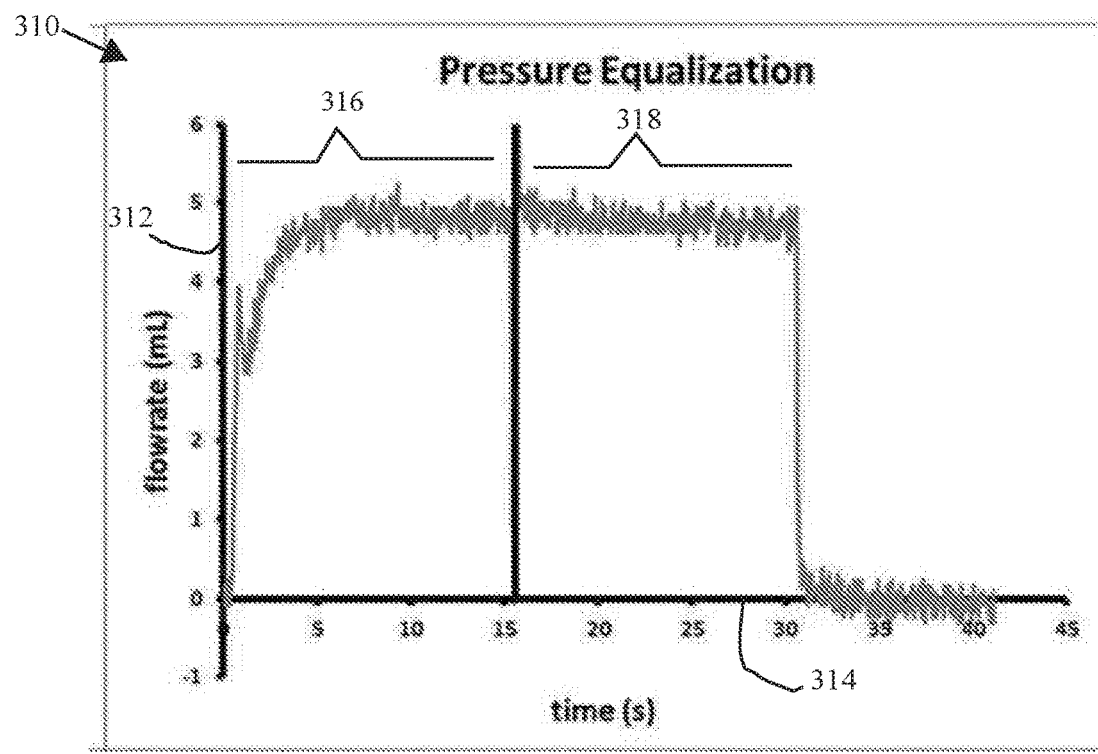
FIG. 9 is a graph depicting flow rate with respect to time for a fluid injection performed according to the method of FIG. 8.
Figure 10:
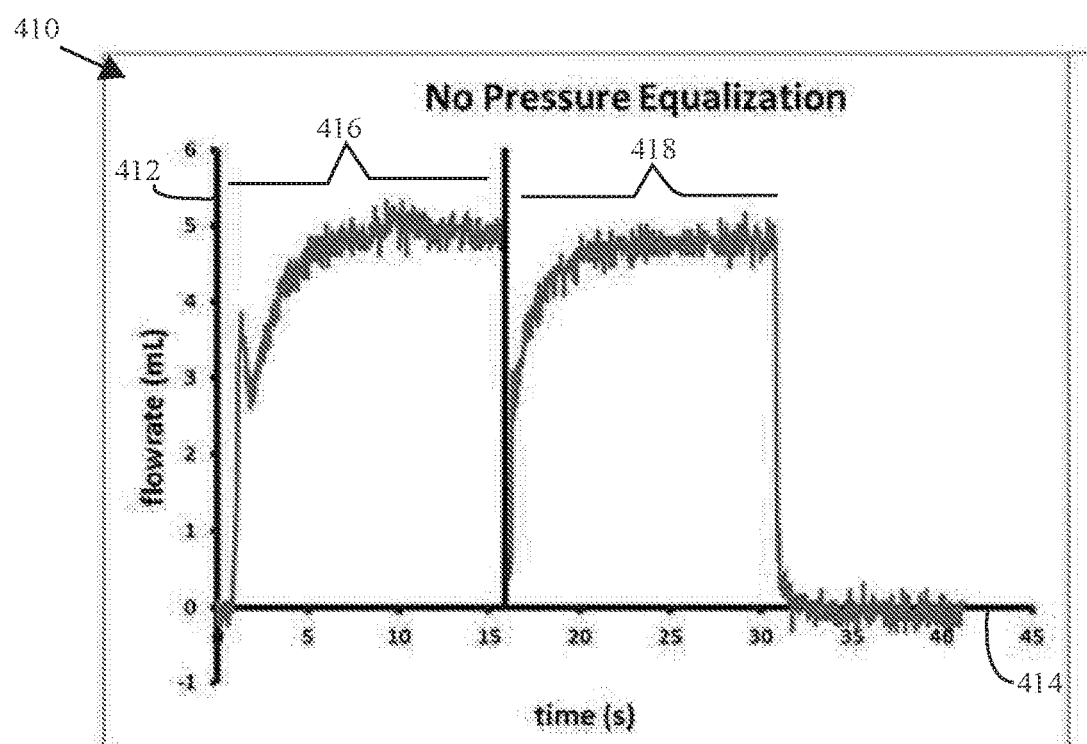
FIG. 10 is a graph depicting flow rate with respect to time for a fluid injection performed without dynamic pressure control.

Graphs showing injection parameters for injections performed using the above described process are shown in FIG. 9 compared to an injection protocol without pressure control, as shown in FIG. 10. Specifically, FIG. 9 shows a graph 310 of flow rate (mL/s) 312 with respect to time 314 for a fluid injection performed using the above-described pressure control process. As shown in FIG. 9, a first phase 316 of the injection occurs between about 0 and 16 seconds. After a short ramp time for first phase 316 of about 5 seconds, the flow rate stabilizes at about 5 mL/s in item 316. In some examples, ramp time can be removed by pre-pressurizing the syringe during or prior to the first phase. A second phase of the injection 318 occurs between about 16 seconds and 30 seconds. A flow rate of about 5 mL/s is provided during the entire second phase 318. In particular, it is noted that, as a result of the above-describe pressure control process, no ramp time is required before the flow rate stabilizes. Instead, a substantially continuous flow of fluid at about 5 mL/s is provided during the transition from the first phase to the second phase and throughout the second phase of the injection.

FIG. 10 shows a graph 410 of flow rate (mL/s) 412 with respect to time 414 for a multiphase injection without pressure control. As shown in the graph 410, a first phase 416 of the injection occurs between about 0 seconds and 16 seconds. As was the case in FIG. 9, the first phase 416 includes about a 5 second ramp time and then flow rate stabilizes at about 5 mL/s. The second phase 418 of the injection occurs between about 16 seconds and 30 seconds. Unlike in the previous example, the second phase 418 includes a ramp time between about 16 seconds and 20 seconds. After the ramp time, the flow rate stabilizes at about 5 mL/s. As shown by the graph 410, without pressure control, a ramp timed or discontinuity occurs between the first phase 416 and the second phase 418. Such a discontinuity is undesirable as it may result in lower image enhancement for diagnostic images and movement of the catheter (momentum changes). In addition, maintaining a substantially constant flow rate across the phase transition is believed to be a more efficient use of contrast volume.

Figure 11:
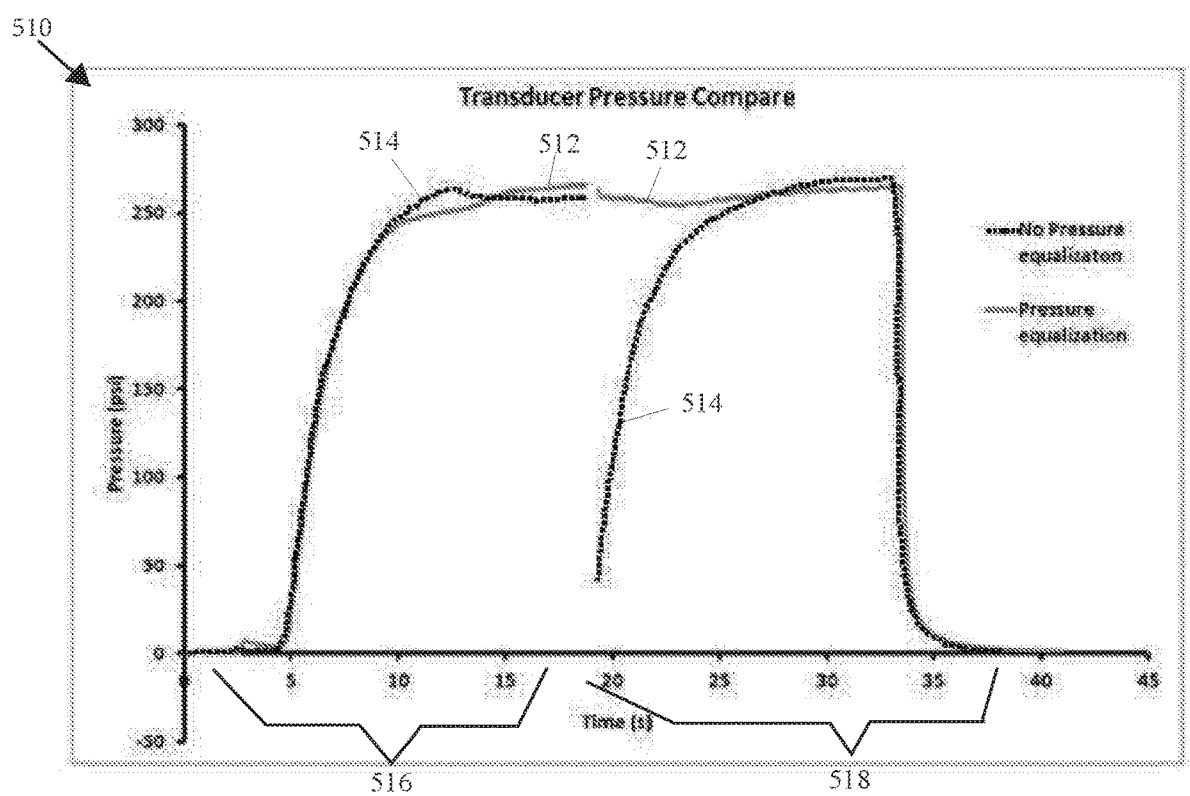
FIG. 11 is a graph depicting pressure with respect to time for injections performed with pressure control and without pressure control.

FIG. 11 is a graph 510 showing pressure (psi) measured by a pressure transducer in a fluid conduit or tubing set with respect to time. The first line 512 shows change in pressure over time for an injection with pressure control. As also shown in FIG. 9, when pressure control is provided, after a short ramp time of about 5 seconds for the first phase 516, fluid is delivered with a substantially constant pressure, as shown by line 512, without a discontinuity or pressure drop between phases 516, 518. In contrast, line 514 shows pressure with respect to time for an injection without pressure control. As shown by line 514, pressure during the first phase 516 of the injection stabilizes at about 250 psi. However, pressure during the second phase 518 of the injection begins at about 50 psi and increases to 250 psi between about 20 seconds and 27 seconds. As such, line 514 in graph 510 shows the discontinuity or substantial pressure drop between phases of the multiphase injection, which is avoided when pressure control is provided. This discontinuity may result in cross contamination if both reservoirs are open to the patient line as well as the flow rate discontinuity observed in FIGS. 9 and 10.

Although the disclosure has been described in detail for the purpose of illustration based on what is currently considered to be the most practical and preferred examples, it is to be understood that such detail is solely for that purpose and that the disclosure is not limited to the disclosed examples, but, on the contrary, is intended to cover modifications and equivalent arrangements. For example, it is to be understood that the present disclosure contemplates that, to the extent possible, one or more features of any example can be combined with one or more features of any other example.

The invention claimed is:

1. A method for dynamic pressure control in a fluid delivery system having a multiphase fluid delivery system comprising at least a first fluid reservoir configured for containing a first fluid, at least a second fluid reservoir configured for containing a second fluid, a fluid conduit for conducting the first fluid from the first reservoir and the second fluid from the second reservoir to a patient, a first valve between the first fluid reservoir and the fluid conduit, a second valve between the second fluid reservoir and the fluid conduit, and a fluid injector comprising at least a first drive member for expelling the first fluid from the first reservoir and at least a second drive member for expelling the second fluid from the second reservoir, wherein the first fluid reservoir is independently in selective fluid communication with the fluid conduit by the first valve, and wherein the second fluid reservoir is independently in selective fluid communication with the fluid conduit by the second valve, the method comprising:

advancing the first drive member to expel the first fluid from the first reservoir into the conduit during a first injection phase while maintaining the second fluid reservoir in fluid isolation from the fluid conduit via the second valve, wherein the first fluid is pressurized to a first fluid pressure;

measuring the first fluid pressure during the first injection phase to provide a target value, wherein the target value is based on the measured first fluid pressure of the first injection phase;

while the second reservoir is in fluid isolation from the conduit, advancing or retracting the second drive member to increase or decrease a second fluid pressure of the second fluid in the second reservoir to the target value;

placing the second reservoir in fluid communication with the conduit by opening the second valve while maintaining the second fluid pressure at the target value; and advancing the second drive member to expel the second fluid from the second reservoir into the conduit while maintaining the second fluid pressure at the target value.

2. The method of claim 1, further comprising isolating the first reservoir from fluid communication with the conduit prior to advancing the second drive member to expel the second fluid from the second reservoir into the conduit.

3. The method of claim 1, wherein the target value is substantially equal to the first fluid pressure.

4. The method of claim 1, wherein the target value is greater than the first fluid pressure.

5. The method of claim 1, wherein the target value is less than the first fluid pressure.

6. The method of claim 1, wherein advancing the second drive member to expel the second fluid from the second reservoir further comprises continuing to advance the first drive member to expel the first fluid from the first reservoir to provide a dual flow fluid delivery of a predetermined ratio of the first fluid and the second fluid.

7. The method of claim 6, further comprising adjusting the first fluid pressure and the second fluid pressure to provide the dual flow fluid delivery, wherein the predetermined ratio is a specified ratio ranging from 1:99 of the first fluid to the second fluid to 99:1 of the first fluid to the second fluid.

8. The method of claim 1, wherein the first fluid comprises an imaging contrast media and the second fluid comprises saline.

9. The method of claim 1, wherein the first fluid reservoir and the second fluid reservoir are fluid reservoirs independently selected from a group consisting of a syringe, a peristaltic pump, and a compressible bag.

10. The method of claim 9, wherein at least one of the first fluid reservoir and the second fluid reservoir is a syringe.

11. The method of claim 1, further comprising at least one third fluid reservoir in selectable fluid communication with the conduit and operatively engaged with at least one third drive member of the fluid injector for expelling at least a third fluid into the conduit.

12. The method of claim 1, wherein each of the first and second valves comprises a first fill position wherein the first and second fluid reservoirs are in fluid communication with a respective fluid container but in fluid isolation with the conduit, a second closed position wherein the first and second fluid reservoirs are in fluid isolation with the respective fluid container and the conduit, and a third delivery position where the first and second fluid reservoirs are in fluid communication with the conduit but in fluid isolation with the respective fluid container.

13. The method of claim 1, wherein each of the first and second valves is operatively controlled by a processor of the fluid injector.

14. A fluid delivery system configured for dynamic pressure equalization during a multiphase/multi-fluid injection, comprising:

at least a first reservoir configured for containing a first fluid;

at least a second reservoir configured for containing a second fluid;

a conduit connected to the first reservoir and the second reservoir for conducting fluid from the first and second reservoirs to a patient;

a first valve between the first fluid reservoir and the fluid conduit, and a second valve between the second fluid reservoir and the fluid conduit a fluid injector comprising at least a first drive member for expelling the first fluid from the first reservoir and at least a second drive member for expelling the second fluid from the second reservoir, wherein the first fluid reservoir is independently in selective fluid communication with the fluid conduit by the first valve, and wherein the second fluid reservoir is independently in selective fluid communication with the fluid conduit by the second valve; and a controller in electronic communication with the fluid injector comprising computer readable memory containing instructions that, when executed by the controller, causes the controller to:

instruct the injector to advance the first drive member to expel the first fluid from the first reservoir during a first injection phase, wherein the first fluid is pressurized to a first fluid pressure;

measure the first fluid pressure during the first injection phase to provide a target value while maintaining the second fluid reservoir in fluid isolation from the fluid conduit via the second valve, wherein the target value is based on the measured first fluid pressure of the first injection phase;

while the second reservoir is in fluid isolation from the conduit, instruct the injector to advance the second drive member to increase a second fluid pressure of the second fluid in the second reservoir to the target value;

instruct the injector to place the second reservoir in fluid communication with the conduit by opening the second valve while maintaining the second fluid pressure at the target value; and instruct the injector to advance the second drive member to expel the second fluid from the second reservoir into the conduit while maintaining the second fluid pressure at the target value.

15. The fluid delivery system of claim 14, wherein the controller comprises further computer readable memory containing instructions that, when executed by the controller, causes the controller to:

instruct the injector to isolate the first fluid reservoir from fluid communication with the conduit prior to instructing the injector to advance the second drive member to expel the second fluid from the second reservoir into the conduit.

16. The fluid delivery system of claim 14, wherein the controller comprises further computer readable memory containing instructions that, when executed by the controller, causes the controller to:

concurrent with instructing the injector to advance the second drive member to expel the second fluid, instruct the injector to continue to advance the first drive member to expel the first fluid from the first reservoir to provide a dual flow fluid delivery of a predetermined ratio of the first fluid and the second fluid.

17. The fluid delivery system of claim 16, wherein the controller comprises further computer readable memory containing instructions that, when executed by the controller, causes the controller to:

during the dual flow fluid delivery, instruct the fluid injector to adjust the first fluid pressure and the second fluid pressure to provide the dual flow fluid delivery, wherein the predetermined ratio is a specified ratio ranging from 1:99 of the first fluid to the second fluid to 99:1 of the first fluid to the second fluid.

18. The fluid delivery system of claim 14, wherein the first fluid reservoir and the second fluid reservoir are fluid reservoirs independently selected from a group consisting of a syringe, a peristaltic pump, and a compressible bag.

19. The fluid delivery system of claim 18, wherein at least one of the first fluid reservoir and the second fluid reservoir is a syringe.

20. The fluid delivery system of claim 14, wherein the fluid injector further comprises at least one third fluid reservoir in selectable fluid communication with the conduit and operatively engaged with at least one third drive member of the fluid injector for expelling at least a third fluid into the conduit.

21. The fluid delivery system of claim 14, wherein each of the first and second valves comprises a first fill position wherein the first and second fluid reservoirs are in fluid communication with a respective fluid container but in fluid isolation with the conduit, a second closed position wherein the first and second fluid reservoirs are in fluid isolation with the respective fluid container and the conduit, and a third delivery position where the first and second fluid reservoirs are in fluid communication with the conduit but in fluid isolation with the respective fluid container.

22. The fluid delivery system of claim 14, wherein each of the first and second valves is operatively controlled by a processor of the fluid injector.

\* \* \* \* \*

UNITED STATES PATENT AND TRADEMARK OFFICE
CERTIFICATE OF CORRECTION

PATENT NO. : 11,779,702 B2
APPLICATION NO. : 16/621289
DATED : October 10, 2023
INVENTOR(S) : Barone et al.

It is certified that error appears in the above-identified patent and that said Letters Patent is hereby corrected as shown below:

In the Specification

In Column 3, Line 37, delete "that" and insert -- than --, therefor.
In Column 6, Line 35, delete "any of" and insert -- any one of --, therefor.
In Column 6, Line 39, delete "any of" and insert -- any one of --, therefor.
In Column 10, Line 47, delete "to within" and insert -- to be within --, therefor.
In Column 13, Line 63, delete "volume saline" and insert -- volume of saline --, therefor.
In Column 14, Line 3, delete "volume saline" and insert -- volume of saline --, therefor.
In Column 15, Lines 35-36, delete "described in described in" and insert -- described in --, therefor.
In Column 15, Line 61, delete "of the a" and insert -- of the --, therefor.
In Column 18, Line 2, delete "in in" and insert -- in --, therefor.
In Column 18, Line 2, delete "of least" and insert -- of at least --, therefor.
In Column 18, Line 19, delete "that" and insert -- than --, therefor.
In Column 22, Line 33, delete "plunger the" and insert -- plunger to the --, therefor.
In Column 22, Line 62, delete "which" and insert -- while --, therefor.

In the Claims

In Column 26, Line 42, in Claim 14, delete "conduit" and insert -- conduit; --, therefor.

Signed and Sealed this
Fifth Day of March, 2024

Katherine Kelly Vidal
*Director of the United States Patent and Trademark Office*